US 9,180,271 B2

(12) United States Patent
Guo et al.

(10) Patent No.: US 9,180,271 B2
(45) Date of Patent: Nov. 10, 2015

(54) RESPIRATORY THERAPY DEVICE HAVING STANDARD AND OSCILLATORY PEP WITH NEBULIZER

(75) Inventors: Mike Yang Chang Guo, Singapore (SG); Soo Yao Jee, Singapore (SG); Radhakrishnan Nair Oravielil Kamalashi, Singapore (SG)

(73) Assignee: Hill-Rom Services Pte. Ltd., Singapore (SG)

( * ) Notice: Subject to any disclaimer, the term of this patent is extended or adjusted under 35 U.S.C. 154(b) by 787 days.

(21) Appl. No.: 13/411,679

(22) Filed: Mar. 5, 2012

(65) Prior Publication Data

US 2013/0228174 A1    Sep. 5, 2013

(51) Int. Cl.
  *A61M 11/00*   (2006.01)
  *A61M 16/00*   (2006.01)
  *A61M 16/20*   (2006.01)
  *A61M 16/08*   (2006.01)

(52) U.S. Cl.
  CPC ....... *A61M 16/0816* (2013.01); *A61M 16/0006* (2014.02); *A61M 16/0833* (2014.02); *A61M 16/20* (2013.01); *A61M 11/00* (2013.01); *A61M 16/208* (2013.01)

(58) Field of Classification Search
  CPC ............. A61M 16/0816; A61M 16/0833; A61M 16/0006; A61M 16/20; A61M 11/00; A61M 16/208; A61M 15/0013; A61M 15/0018
  USPC ............ 128/205.24, 200.14, 200.19, 200.24, 128/203.12; 137/625.4, 625.41, 625.44, 137/625, 46
  See application file for complete search history.

(56) References Cited

U.S. PATENT DOCUMENTS

| | | | |
|---|---|---|---|
| 2,040,930 A * | 5/1936 | Frisch | ............ 137/625.44 |
| 2,098,280 A | 11/1937 | Dornseif | |
| 3,628,280 A | 12/1971 | Nave | |
| 3,710,780 A | 1/1973 | Milch | |
| 3,863,914 A | 2/1975 | OConnor | |
| 3,908,987 A | 9/1975 | Boehringer | |
| 3,922,525 A | 11/1975 | Kozak et al. | |
| 3,936,048 A | 2/1976 | Dunlap et al. | |
| 3,949,737 A | 4/1976 | Nielsen | |
| 3,949,984 A | 4/1976 | Navara | |
| 3,958,565 A | 5/1976 | Wright | |

(Continued)

FOREIGN PATENT DOCUMENTS

| | | |
|---|---|---|
| EP | 1 103 287 A2 | 5/2001 |
| EP | 1 435 251 A1 | 7/2004 |

(Continued)

OTHER PUBLICATIONS

Expand a Lung Breathing Resistance Exerciser web advertisement, www.expand-a-lung.com , Copyright 2006-2008, Expand-a-Lung, printed Nov. 11, 2008 (2 pages).

(Continued)

*Primary Examiner* — Justine Yu
*Assistant Examiner* — Douglas Sul
(74) *Attorney, Agent, or Firm* — Barnes & Thornburg LLP

(57) ABSTRACT

A respiratory therapy device has both a standard positive expiratory pressure (PEP) device and an oscillatory PEP device packaged together. A manually operable member is movable to select which of the standard and oscillatory PEP device is placed in communication with a patient's airway. A nebulizer connector may also be provided for connection of a nebulizer.

43 Claims, 10 Drawing Sheets

(56) References Cited

U.S. PATENT DOCUMENTS

| | | |
|---|---|---|
| 3,972,326 A | 8/1976 | Brawn |
| 3,977,395 A | 8/1976 | Brawn |
| 3,977,399 A | 8/1976 | Brawn |
| D242,956 S | 1/1977 | Miller et al. |
| 4,010,946 A | 3/1977 | Miller |
| 4,025,070 A | 5/1977 | McGill et al. |
| 4,037,836 A | 7/1977 | Puderbaugh et al. |
| 4,041,935 A | 8/1977 | Garbe |
| 4,054,134 A | 10/1977 | Kritzer |
| 4,060,074 A | 11/1977 | Russo |
| 4,062,358 A | 12/1977 | Kritzer |
| 4,086,918 A | 5/1978 | Russo |
| 4,094,508 A | 6/1978 | Kirsch |
| 4,096,855 A | 6/1978 | Fleury, Jr. |
| 4,114,607 A | 9/1978 | Russo |
| 4,114,608 A | 9/1978 | Russo |
| 4,114,616 A | 9/1978 | Brawn |
| 4,121,583 A | 10/1978 | Chen |
| 4,138,105 A | 2/1979 | Hunger et al. |
| 4,143,872 A | 3/1979 | Havstad et al. |
| 4,144,883 A | 3/1979 | Grieshaber |
| 4,158,360 A | 6/1979 | Adams |
| 4,170,228 A | 10/1979 | Elson et al. |
| 4,171,804 A | 10/1979 | Thead, Jr. |
| 4,176,663 A | 12/1979 | Hewlett |
| 4,182,347 A | 1/1980 | Russo |
| 4,182,599 A | 1/1980 | Eyrick et al. |
| 4,183,361 A | 1/1980 | Russo |
| D254,324 S | 2/1980 | Thead, Jr. |
| D254,443 S | 3/1980 | Adams |
| 4,221,381 A | 9/1980 | Ericson |
| 4,231,375 A | 11/1980 | Boehringer et al. |
| 4,232,683 A | 11/1980 | Bartholomew et al. |
| 4,233,990 A | 11/1980 | Yardley |
| 4,241,739 A | 12/1980 | Elson |
| 4,241,740 A | 12/1980 | Brown |
| 4,245,633 A | 1/1981 | Erceg |
| 4,282,883 A | 8/1981 | Yerushalmy |
| 4,284,083 A | 8/1981 | Lester |
| 4,291,704 A | 9/1981 | Petty et al. |
| 4,299,236 A | 11/1981 | Poirier |
| 4,301,810 A | 11/1981 | Belman |
| 4,323,078 A | 4/1982 | Heimlich |
| 4,324,260 A | 4/1982 | Puderbaugh |
| 4,327,740 A | 5/1982 | Shuman |
| 4,327,741 A | 5/1982 | Watson et al. |
| 4,333,452 A | 6/1982 | Au |
| 4,345,605 A | 8/1982 | Gereg |
| 4,347,853 A | 9/1982 | Gereg et al. |
| 4,363,328 A | 12/1982 | Poirier et al. |
| D269,124 S | 5/1983 | McCombs et al. |
| 4,391,283 A | 7/1983 | Sharpless et al. |
| 4,403,616 A | 9/1983 | King |
| 4,421,113 A | 12/1983 | Gedeon et al. |
| 4,425,923 A | 1/1984 | Gordon et al. |
| 4,436,090 A | 3/1984 | Darling |
| 4,441,505 A | 4/1984 | Edwards et al. |
| 4,441,506 A | 4/1984 | McCombs et al. |
| 4,444,202 A | 4/1984 | Rubin et al. |
| 4,470,412 A | 9/1984 | Nowacki et al. |
| 4,473,082 A | 9/1984 | Gereg |
| 4,487,207 A | 12/1984 | Fitz |
| 4,495,944 A | 1/1985 | Brisson et al. |
| 4,499,905 A | 2/1985 | Greenberg et al. |
| 4,506,883 A | 3/1985 | Rathbun |
| 4,533,137 A | 8/1985 | Sonne |
| 4,534,343 A | 8/1985 | Nowacki et al. |
| 4,579,124 A | 4/1986 | Jentges |
| 4,585,012 A | 4/1986 | Rumburg |
| 4,595,196 A | 6/1986 | Muchisky et al. |
| 4,601,465 A | 7/1986 | Roy |
| 4,619,532 A | 10/1986 | Schmidt, III |
| 4,621,631 A | 11/1986 | Pâques et al. |
| 4,632,610 A | 12/1986 | Hougen |
| 4,634,117 A | 1/1987 | Kramer |
| 4,635,647 A | 1/1987 | Choksi |
| 4,638,812 A | 1/1987 | Hakkinen |
| 4,654,009 A | 3/1987 | Greene |
| D293,613 S | 1/1988 | Wingler |
| 4,739,987 A | 4/1988 | Nicholson |
| 4,766,894 A | 8/1988 | Legrand et al. |
| 4,767,785 A | 8/1988 | Georgieff |
| 4,770,413 A | 9/1988 | Green |
| 4,787,627 A | 11/1988 | Daubenspeck |
| 4,796,614 A | 1/1989 | Nowacki et al. |
| 4,809,692 A | 3/1989 | Nowacki et al. |
| 4,813,819 A | 3/1989 | Hougen |
| 4,821,713 A | 4/1989 | Bauman |
| 4,823,828 A | 4/1989 | McGinnis |
| 4,824,105 A | 4/1989 | Goldenberg |
| 4,832,015 A | 5/1989 | Nowacki et al. |
| 4,838,257 A | 6/1989 | Hatch |
| 4,854,574 A | 8/1989 | Larson et al. |
| 4,889,137 A | 12/1989 | Kolobow |
| 4,915,103 A | 4/1990 | Visveshwara et al. |
| 4,938,210 A | 7/1990 | Shene |
| 4,951,661 A | 8/1990 | Sladek |
| 4,952,102 A | 8/1990 | Hougen |
| 4,964,404 A | 10/1990 | Stone |
| 4,967,742 A | 11/1990 | Theodorou |
| 4,973,047 A | 11/1990 | Norell |
| 4,981,295 A | 1/1991 | Belman et al. |
| 4,982,735 A | 1/1991 | Yagata et al. |
| 4,986,269 A | 1/1991 | Hakkinen |
| 5,002,050 A | 3/1991 | McGinnis |
| 5,012,803 A | 5/1991 | Foley et al. |
| 5,012,804 A | 5/1991 | Foley et al. |
| 5,018,517 A | 5/1991 | Liardet |
| 5,027,809 A | 7/1991 | Robinson |
| 5,042,467 A | 8/1991 | Foley |
| 5,054,478 A | 10/1991 | Grychowski et al. |
| 5,060,655 A | 10/1991 | Rudolph |
| 5,067,707 A | 11/1991 | Kohnke |
| 5,069,449 A | 12/1991 | Wardwell |
| 5,072,729 A | 12/1991 | DeVries |
| 5,074,295 A | 12/1991 | Willis |
| 5,078,131 A | 1/1992 | Foley |
| 5,099,833 A * | 3/1992 | Michaels ................ 128/200.14 |
| 5,107,830 A | 4/1992 | Younes |
| 5,127,400 A | 7/1992 | DeVries et al. |
| 5,129,390 A | 7/1992 | Chopin et al. |
| 5,133,700 A | 7/1992 | Braathen |
| 5,134,996 A | 8/1992 | Bell |
| 5,145,296 A | 9/1992 | Hougen |
| 5,148,802 A | 9/1992 | Sanders et al. |
| 5,150,291 A | 9/1992 | Cummings et al. |
| 5,154,167 A | 10/1992 | Hepburn |
| 5,165,393 A | 11/1992 | Kawaguchi |
| 5,193,529 A | 3/1993 | Labaere |
| 5,203,650 A | 4/1993 | McCourtney |
| 5,245,991 A | 9/1993 | Kawaguchi |
| 5,246,010 A | 9/1993 | Gazzara et al. |
| 5,253,651 A | 10/1993 | Stockwell et al. |
| 5,255,687 A | 10/1993 | McKenna |
| D340,975 S | 11/1993 | Sladek |
| 5,261,394 A | 11/1993 | Mulligan et al. |
| 5,277,195 A | 1/1994 | Williams |
| 5,303,699 A | 4/1994 | Bonassa et al. |
| 5,307,795 A | 5/1994 | Whitwam et al. |
| 5,309,906 A | 5/1994 | LaBombard |
| 5,315,990 A | 5/1994 | Mondry |
| 5,342,260 A | 8/1994 | Markland |
| 5,355,873 A | 10/1994 | Del Bon et al. |
| 5,357,975 A | 10/1994 | Kraemer et al. |
| 5,370,113 A | 12/1994 | Parsons |
| 5,372,118 A | 12/1994 | Schmidt, III et al. |
| 5,373,851 A | 12/1994 | Reinhold, Jr. et al. |
| 5,392,768 A | 2/1995 | Johansson et al. |
| 5,393,281 A | 2/1995 | Chen |
| 5,394,866 A | 3/1995 | Ritson et al. |
| 5,398,676 A | 3/1995 | Press et al. |
| 5,400,777 A | 3/1995 | Olsson et al. |
| 5,404,871 A | 4/1995 | Goodman et al. |
| 5,413,110 A | 5/1995 | Cummings et al. |

(56) References Cited

U.S. PATENT DOCUMENTS

| | | |
|---|---|---|
| 5,413,112 A | 5/1995 | Jansen et al. |
| 5,415,161 A | 5/1995 | Ryder |
| 5,415,165 A | 5/1995 | Fiddian-Green |
| 5,423,313 A | 6/1995 | Olsson et al. |
| 5,433,193 A | 7/1995 | Sanders et al. |
| 5,433,216 A | 7/1995 | Sugrue et al. |
| 5,439,430 A | 8/1995 | Rubens et al. |
| D362,500 S | 9/1995 | Cook et al. |
| 5,449,751 A | 9/1995 | Forssmann et al. |
| 5,451,190 A | 9/1995 | Liardet |
| 5,451,408 A | 9/1995 | Mezei et al. |
| 5,456,251 A | 10/1995 | Fiddian-Green |
| 5,461,934 A | 10/1995 | Budd |
| D365,581 S | 12/1995 | McCourtney |
| 5,474,058 A | 12/1995 | Lix |
| 5,479,920 A | 1/1996 | Piper et al. |
| 5,487,378 A | 1/1996 | Robertson et al. |
| 5,490,498 A | 2/1996 | Faithfull et al. |
| 5,490,502 A | 2/1996 | Rapoport et al. |
| 5,494,028 A | 2/1996 | DeVries et al. |
| 5,507,282 A | 4/1996 | Younes |
| 5,509,404 A | 4/1996 | Lloyd et al. |
| 5,509,870 A | 4/1996 | Lloyd |
| 5,518,002 A | 5/1996 | Wolf et al. |
| 5,522,378 A | 6/1996 | Ritson et al. |
| 5,526,809 A | 6/1996 | Fiddian-Green |
| 5,535,738 A | 7/1996 | Estes et al. |
| 5,535,739 A | 7/1996 | Rapoport et al. |
| 5,540,234 A | 7/1996 | Lalui |
| 5,542,410 A | 8/1996 | Goodman et al. |
| 5,546,933 A | 8/1996 | Rapoport et al. |
| 5,547,440 A | 8/1996 | Rubens et al. |
| 5,549,106 A | 8/1996 | Gruenke et al. |
| 5,551,419 A | 9/1996 | Froehlich et al. |
| 5,555,880 A | 9/1996 | Winter et al. |
| 5,558,085 A | 9/1996 | Rubsamen et al. |
| 5,558,086 A | 9/1996 | Smith et al. |
| 5,560,353 A | 10/1996 | Willemot et al. |
| 5,560,371 A | 10/1996 | Carvalho da Silva |
| 5,569,122 A | 10/1996 | Cegla |
| 5,570,682 A | 11/1996 | Johnson |
| 5,572,993 A | 11/1996 | Kurome et al. |
| 5,575,283 A | 11/1996 | Sjoestrand |
| 5,582,163 A | 12/1996 | Bonassa |
| 5,595,166 A | 1/1997 | Schmidt, III et al. |
| 5,598,838 A | 2/1997 | Servidio et al. |
| 5,598,839 A * | 2/1997 | Niles et al. ............... 128/205.23 |
| 5,601,078 A | 2/1997 | Schaller et al. |
| 5,613,489 A | 3/1997 | Miller et al. |
| 5,613,497 A | 3/1997 | DeBush |
| 5,617,846 A | 4/1997 | Graetz et al. |
| 5,617,847 A | 4/1997 | Howe |
| 5,622,162 A | 4/1997 | Johansson et al. |
| 5,626,131 A | 5/1997 | Chua et al. |
| 5,627,324 A | 5/1997 | Shene |
| 5,632,269 A | 5/1997 | Zdrojkowski |
| 5,632,298 A | 5/1997 | Artinian |
| 5,642,730 A | 7/1997 | Baran |
| 5,645,049 A | 7/1997 | Foley et al. |
| 5,647,351 A | 7/1997 | Weismann et al. |
| 5,649,533 A | 7/1997 | Oren |
| 5,655,516 A | 8/1997 | Goodman et al. |
| 5,655,521 A | 8/1997 | Faithfull et al. |
| 5,658,221 A | 8/1997 | Hougen |
| 5,660,166 A | 8/1997 | Lloyd et al. |
| 5,664,562 A | 9/1997 | Bourdon |
| 5,665,861 A | 9/1997 | Forssmann et al. |
| 5,685,296 A | 11/1997 | Zdrojkowski et al. |
| 5,686,409 A | 11/1997 | McFadden et al. |
| 5,694,923 A | 12/1997 | Hete et al. |
| 5,697,364 A | 12/1997 | Chua et al. |
| 5,730,120 A | 3/1998 | Yonkers, Jr. |
| 5,740,796 A | 4/1998 | Skog |
| 5,740,797 A | 4/1998 | Dickson |
| 5,743,252 A | 4/1998 | Rubsamen et al. |
| 5,749,368 A | 5/1998 | Kase |
| 5,752,509 A | 5/1998 | Lachmann et al. |
| 5,755,640 A | 5/1998 | Frolov et al. |
| 5,771,884 A | 6/1998 | Yarnall et al. |
| 5,788,631 A | 8/1998 | Fiddian-Green |
| 5,791,339 A | 8/1998 | Winter |
| 5,794,615 A | 8/1998 | Estes |
| 5,797,393 A | 8/1998 | Kohl |
| 5,799,652 A | 9/1998 | Kotliar |
| 5,803,065 A | 9/1998 | Zdrojkowski et al. |
| 5,803,066 A | 9/1998 | Rapoport et al. |
| 5,813,397 A | 9/1998 | Goodman et al. |
| 5,813,400 A | 9/1998 | Buhlmann et al. |
| 5,816,246 A | 10/1998 | Mirza |
| 5,819,726 A | 10/1998 | Rubsamen et al. |
| 5,823,179 A | 10/1998 | Grychowski et al. |
| 5,829,429 A | 11/1998 | Hughes |
| 5,834,419 A | 11/1998 | McFadden et al. |
| 5,839,434 A | 11/1998 | Enterline |
| 5,848,588 A | 12/1998 | Foley et al. |
| 5,853,003 A | 12/1998 | Faithfull et al. |
| 5,875,777 A | 3/1999 | Eriksson |
| 5,878,743 A | 3/1999 | Zdrojkowski et al. |
| 5,878,744 A | 3/1999 | Pfeiffer |
| 5,881,722 A | 3/1999 | DeVries et al. |
| 5,881,724 A | 3/1999 | Graetz et al. |
| 5,881,772 A | 3/1999 | Bennett |
| 5,890,998 A | 4/1999 | Hougen |
| 5,899,832 A | 5/1999 | Hougen |
| 5,910,071 A | 6/1999 | Hougen |
| 5,915,381 A | 6/1999 | Nord |
| 5,917,014 A | 6/1999 | McFadden et al. |
| 5,921,238 A | 7/1999 | Bourdon |
| 5,927,274 A | 7/1999 | Servidio et al. |
| 5,931,159 A | 8/1999 | Suzuki et al. |
| 5,931,162 A | 8/1999 | Christian |
| 5,931,163 A | 8/1999 | Stegmann et al. |
| 5,937,853 A | 8/1999 | Strom |
| 5,937,854 A | 8/1999 | Stenzler |
| 5,937,855 A | 8/1999 | Zdrojkowski et al. |
| 5,937,857 A | 8/1999 | Caterini et al. |
| 5,939,525 A | 8/1999 | McFadden et al. |
| 5,954,049 A | 9/1999 | Foley et al. |
| 5,957,124 A | 9/1999 | Lloyd et al. |
| 5,960,792 A | 10/1999 | Lloyd et al. |
| 5,964,223 A | 10/1999 | Baran |
| 5,984,873 A | 11/1999 | Crumb et al. |
| 5,988,160 A | 11/1999 | Foley et al. |
| 6,003,511 A | 12/1999 | Fukunaga et al. |
| 6,006,748 A | 12/1999 | Hollis |
| 6,009,871 A | 1/2000 | Kiske et al. |
| 6,010,453 A | 1/2000 | Fiddian-Green |
| 6,010,460 A | 1/2000 | McNaughton |
| 6,014,972 A | 1/2000 | Sladek |
| 6,024,090 A | 2/2000 | Gonda et al. |
| 6,029,660 A | 2/2000 | Calluaud et al. |
| 6,029,664 A | 2/2000 | Zdrojkowski et al. |
| 6,032,667 A | 3/2000 | Heinonen |
| 6,035,896 A | 3/2000 | Liardet |
| 6,038,913 A | 3/2000 | Gustafsson et al. |
| 6,039,042 A | 3/2000 | Sladek |
| 6,042,509 A | 3/2000 | Wu et al. |
| 6,044,841 A | 4/2000 | Verdun et al. |
| 6,058,932 A | 5/2000 | Hughes |
| 6,073,630 A | 6/2000 | Adahan |
| 6,076,519 A | 6/2000 | Johnson |
| 6,079,412 A | 6/2000 | Meier et al. |
| 6,079,413 A | 6/2000 | Baran |
| 6,082,357 A | 7/2000 | Bates et al. |
| 6,082,358 A | 7/2000 | Scarrott et al. |
| 6,083,141 A | 7/2000 | Hougen |
| 6,085,746 A | 7/2000 | Fox |
| 6,089,105 A | 7/2000 | Ricciardelli |
| D429,330 S | 8/2000 | Hoenig |
| 6,095,140 A | 8/2000 | Poon et al. |
| 6,098,620 A | 8/2000 | Lloyd et al. |
| 6,102,038 A | 8/2000 | DeVries |
| 6,102,042 A | 8/2000 | Hete et al. |
| 6,105,575 A | 8/2000 | Estes et al. |

(56) References Cited

U.S. PATENT DOCUMENTS

| | | | |
|---|---|---|---|
| 6,119,684 A | 9/2000 | Nohl et al. |
| 6,119,687 A | 9/2000 | Faithfull et al. |
| 6,129,086 A | 10/2000 | Gzybowski et al. |
| 6,131,853 A | 10/2000 | Bauer et al. |
| 6,135,106 A | 10/2000 | Dirks et al. |
| 6,142,339 A | 11/2000 | Blacker et al. |
| 6,161,499 A | 12/2000 | Sun et al. |
| 6,161,724 A | 12/2000 | Blacker et al. |
| 6,165,105 A | 12/2000 | Boutellier et al. |
| 6,167,881 B1 | 1/2001 | Hughes |
| 6,182,657 B1 | 2/2001 | Brydon et al. |
| 6,186,142 B1 | 2/2001 | Schmidt et al. |
| 6,192,876 B1 | 2/2001 | Denyer et al. |
| D439,534 S | 3/2001 | Scarrott et al. |
| 6,196,222 B1 | 3/2001 | Heinonen et al. |
| 6,202,643 B1 | 3/2001 | Sladek |
| D440,651 S | 4/2001 | Foran et al. |
| D441,070 S | 4/2001 | Niles et al. |
| 6,210,345 B1 | 4/2001 | Van Brunt |
| 6,213,119 B1 | 4/2001 | Brydon et al. |
| 6,240,919 B1 | 6/2001 | MacDonald et al. |
| 6,253,766 B1 | 7/2001 | Niles et al. |
| 6,257,234 B1 | 7/2001 | Sun |
| 6,273,087 B1 | 8/2001 | Boussignac et al. |
| 6,280,123 B1 | 8/2001 | Gill |
| D447,432 S | 9/2001 | Scarrott et al. |
| 6,283,119 B1 | 9/2001 | Bourdon |
| 6,283,122 B1 | 9/2001 | Adahan |
| 6,283,365 B1 | 9/2001 | Bason |
| 6,289,892 B1 | 9/2001 | Faithfull et al. |
| 6,293,279 B1 | 9/2001 | Schmidt et al. |
| 6,302,105 B1 | 10/2001 | Wickham et al. |
| 6,305,372 B1 | 10/2001 | Servidio |
| 6,305,374 B1 | 10/2001 | Zdrojkowski et al. |
| D450,381 S | 11/2001 | Weinstein et al. |
| 6,328,037 B1 | 12/2001 | Scarrott et al. |
| 6,334,064 B1 | 12/2001 | Fiddian-Green |
| 6,336,453 B1 | 1/2002 | Scarrott et al. |
| 6,340,025 B1 | 1/2002 | Van Brunt |
| 6,345,617 B1 | 2/2002 | Engelbreth et al. |
| 6,345,619 B1 | 2/2002 | Finn |
| 6,360,740 B1 | 3/2002 | Ward et al. |
| 6,360,745 B1 | 3/2002 | Wallace et al. |
| D456,292 S | 4/2002 | Scarrott et al. |
| 6,363,933 B1 | 4/2002 | Berthon-Jones |
| 6,367,474 B1 | 4/2002 | Berthon-Jones et al. |
| 6,371,115 B1 | 4/2002 | Cewers et al. |
| 6,378,520 B1 | 4/2002 | Davenport |
| 6,379,316 B1 | 4/2002 | Van Brunt et al. |
| 6,390,088 B1 | 5/2002 | Nohl et al. |
| 6,397,845 B1 | 6/2002 | Burton |
| 6,401,713 B1 | 6/2002 | Hill et al. |
| 6,405,728 B1 | 6/2002 | Van Hall et al. |
| 6,409,638 B1 | 6/2002 | Huston |
| 6,415,791 B1 | 7/2002 | Van Brunt |
| 6,425,393 B1 | 7/2002 | Lurie et al. |
| 6,431,171 B1 | 8/2002 | Burton |
| 6,435,177 B1 | 8/2002 | Schmidt et al. |
| 6,435,372 B1 | 8/2002 | Blacker et al. |
| 6,439,228 B1 | 8/2002 | Hete et al. |
| 6,450,163 B1 | 9/2002 | Blacker et al. |
| 6,450,969 B1 | 9/2002 | Farr et al. |
| 6,454,680 B1 | 9/2002 | Taimela |
| 6,471,621 B2 | 10/2002 | Horstel et al. |
| 6,484,719 B1 | 11/2002 | Berthon-Jones |
| 6,495,515 B1 | 12/2002 | McFadden et al. |
| 6,500,095 B1 | 12/2002 | Hougen |
| 6,502,572 B1 | 1/2003 | Berthon-Jones et al. |
| 6,514,177 B1 | 2/2003 | Brugger et al. |
| 6,526,970 B2 | 3/2003 | DeVries et al. |
| 6,526,974 B1 | 3/2003 | Brydon et al. |
| 6,526,976 B1 | 3/2003 | Baran |
| 6,530,372 B1 | 3/2003 | Madaus et al. |
| 6,532,956 B2 | 3/2003 | Hill |
| 6,536,433 B1 | 3/2003 | Cewers |
| 6,539,938 B2 | 4/2003 | Weinstein et al. |
| 6,539,940 B2 | 4/2003 | Zdrojkowski et al. |
| 6,543,449 B1 | 4/2003 | Woodring et al. |
| 6,550,473 B1 | 4/2003 | Sladek |
| 6,554,746 B1 | 4/2003 | McConnell et al. |
| 6,557,549 B2 | 5/2003 | Schmidt et al. |
| 6,558,221 B1 | 5/2003 | Yang |
| 6,561,384 B2 | 5/2003 | Blacker et al. |
| 6,568,387 B2 | 5/2003 | Davenport et al. |
| 6,581,595 B1 | 6/2003 | Murdock et al. |
| 6,581,596 B1 * | 6/2003 | Truitt et al. ............... 128/204.21 |
| 6,581,598 B1 | 6/2003 | Foran et al. |
| 6,581,697 B1 | 6/2003 | Giardino |
| 6,581,896 B1 | 6/2003 | Olexovitch |
| 6,588,422 B1 | 7/2003 | Berthon-Jones et al. |
| 6,588,427 B1 | 7/2003 | Carlsen et al. |
| 6,589,933 B1 | 7/2003 | McFadden et al. |
| 6,609,517 B1 | 8/2003 | Estes et al. |
| 6,612,303 B1 | 9/2003 | Grychowski et al. |
| 6,615,831 B1 | 9/2003 | Tuitt et al. |
| 6,622,724 B1 | 9/2003 | Truitt et al. |
| 6,626,175 B2 | 9/2003 | Jafari et al. |
| 6,631,716 B1 | 10/2003 | Robinson et al. |
| 6,631,721 B1 | 10/2003 | Salter et al. |
| 6,644,304 B2 | 11/2003 | Grychowski et al. |
| 6,644,305 B2 | 11/2003 | MacRae et al. |
| 6,651,654 B2 | 11/2003 | Rogacki |
| 6,656,129 B2 | 12/2003 | Niles et al. |
| RE38,407 E | 1/2004 | Mezel et al. |
| 6,672,300 B1 | 1/2004 | Grant |
| 6,679,252 B2 | 1/2004 | Sladek |
| 6,679,258 B1 | 1/2004 | Strom |
| 6,691,579 B2 | 2/2004 | Orr et al. |
| 6,694,969 B1 | 2/2004 | Heinonen et al. |
| 6,694,978 B1 | 2/2004 | Bennarsten |
| 6,702,720 B2 | 3/2004 | Dardik |
| 6,702,769 B1 * | 3/2004 | Fowler-Hawkins ............ 601/46 |
| 6,702,998 B2 | 3/2004 | Conner |
| 6,708,688 B1 | 3/2004 | Rubin et al. |
| 6,708,690 B1 | 3/2004 | Hete et al. |
| D489,129 S | 4/2004 | King et al. |
| 6,718,969 B1 | 4/2004 | Rubin et al. |
| 6,722,362 B2 | 4/2004 | Hete et al. |
| 6,723,024 B2 | 4/2004 | Levine |
| 6,726,598 B1 | 4/2004 | Jarvis et al. |
| D490,519 S | 5/2004 | Pelerossi et al. |
| 6,729,330 B2 | 5/2004 | Scarrott et al. |
| 6,729,334 B1 | 5/2004 | Baran |
| 6,745,760 B2 | 6/2004 | Grychowski et al. |
| 6,748,945 B2 | 6/2004 | Grychowski et al. |
| 6,752,151 B2 | 6/2004 | Hill |
| 6,761,161 B2 | 7/2004 | Scarrott et al. |
| 6,761,165 B2 | 7/2004 | Strickland, Jr. |
| 6,766,800 B2 | 7/2004 | Murdock et al. |
| 6,776,159 B2 | 8/2004 | Pelerossi et al. |
| 6,792,942 B1 | 9/2004 | Ho et al. |
| 6,805,118 B2 | 10/2004 | Brooker et al. |
| 6,805,120 B1 | 10/2004 | Jeffrey et al. |
| 6,814,074 B1 | 11/2004 | Nadjafizadeh et al. |
| 6,814,076 B2 | 11/2004 | Shusterman et al. |
| 6,817,361 B2 | 11/2004 | Berthon-Jones et al. |
| 6,820,613 B2 | 11/2004 | Wenkebach et al. |
| 6,823,866 B2 | 11/2004 | Jafari et al. |
| 6,837,260 B1 | 1/2005 | Kuehn |
| 6,848,443 B2 | 2/2005 | Schmidt et al. |
| 6,851,425 B2 | 2/2005 | Jaffre et al. |
| 6,854,462 B2 | 2/2005 | Berthon-Jones et al. |
| 6,860,265 B1 | 3/2005 | Emerson |
| 6,863,068 B2 | 3/2005 | Jamison et al. |
| 6,866,040 B1 | 3/2005 | Bourdon |
| 6,877,511 B2 | 4/2005 | DeVries et al. |
| 6,880,556 B2 | 4/2005 | Uchiyama et al. |
| 6,889,691 B2 | 5/2005 | Eklund et al. |
| 6,894,155 B2 | 5/2005 | McFadden et al. |
| 6,904,906 B2 | 6/2005 | Salter et al. |
| 6,904,908 B2 | 6/2005 | Bruce et al. |
| 6,907,881 B2 | 6/2005 | Suki et al. |
| 6,910,479 B1 | 6/2005 | Van Brunt |
| 6,914,076 B2 | 7/2005 | Cavazza |

(56) References Cited

U.S. PATENT DOCUMENTS

| | | |
|---|---|---|
| 6,915,705 B1 | 7/2005 | Truitt et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,926,002 B2 | 8/2005 | Scarrott et al. |
| 6,929,003 B2 | 8/2005 | Blacker et al. |
| 6,929,007 B2 | 8/2005 | Emerson |
| 6,932,084 B2 | 8/2005 | Estes et al. |
| 6,935,338 B1 | 8/2005 | Triunfo, Jr. |
| 6,938,619 B1 | 9/2005 | Hickle |
| 6,938,796 B2 | 9/2005 | Blacker et al. |
| 6,948,497 B2 | 9/2005 | Zdrojkowski et al. |
| 6,953,039 B2 | 10/2005 | Scarrott et al. |
| 6,968,741 B2 | 11/2005 | Orr et al. |
| 6,976,491 B2 | 12/2005 | Dagosto |
| 6,984,214 B2 | 1/2006 | Fowler-Hawkins |
| 6,988,498 B2 | 1/2006 | Berthon-Jones et al. |
| 6,988,994 B2 | 1/2006 | Rapoport et al. |
| 6,994,083 B2 | 2/2006 | Foley et al. |
| 6,997,349 B2 | 2/2006 | Blacker et al. |
| 7,000,612 B2 | 2/2006 | Jafari et al. |
| 7,004,164 B2 | 2/2006 | Scarrott |
| 7,007,693 B2 | 3/2006 | Fuhrman et al. |
| 7,011,087 B1 | 3/2006 | Sullivan |
| 7,011,091 B2 | 3/2006 | Hill et al. |
| 7,013,896 B2 | 3/2006 | Schmidt |
| 7,036,500 B2 | 5/2006 | Niles et al. |
| 7,040,318 B2 | 5/2006 | Dascher et al. |
| 7,044,129 B1 | 5/2006 | Truschel et al. |
| 7,059,324 B2 | 6/2006 | Pelerossi et al. |
| 7,077,141 B2 | 7/2006 | Troop |
| 7,080,643 B2 | 7/2006 | Grychowski et al. |
| 7,096,866 B2 | 8/2006 | Be'eri et al. |
| 7,100,530 B2 | 9/2006 | Lu |
| 7,100,607 B2 | 9/2006 | Zdrojkowski et al. |
| 7,101,559 B2 | 9/2006 | McFadden et al. |
| 7,121,277 B2 | 10/2006 | Strom |
| 7,134,434 B2 | 11/2006 | Truitt et al. |
| 7,143,908 B2 | 12/2006 | Blacker et al. |
| 7,159,973 B2 | 1/2007 | Buchanan et al. |
| 7,162,296 B2 | 1/2007 | Leonhardt et al. |
| 7,165,547 B2 | 1/2007 | Truitt et al. |
| 7,174,789 B2 | 2/2007 | Orr et al. |
| 7,178,522 B2 | 2/2007 | Baker et al. |
| 7,186,221 B2 | 3/2007 | Rapoport et al. |
| 7,191,776 B2 | 3/2007 | Niles et al. |
| 7,191,782 B2 | 3/2007 | Madsen |
| 7,191,783 B2 | 3/2007 | Russell |
| 7,201,164 B2 | 4/2007 | Grychowski et al. |
| 7,201,165 B2 | 4/2007 | Bruce et al. |
| 7,210,478 B2 | 5/2007 | Banner et |
| 7,225,807 B2 | 6/2007 | Papania et al. |
| 7,232,417 B2 | 6/2007 | Plante |
| 7,241,269 B2 | 7/2007 | McCawley et al. |
| 7,246,618 B2 | 7/2007 | Habashi |
| 7,267,122 B2 | 9/2007 | Hill |
| 7,270,123 B2 | 9/2007 | Grychowski et al. |
| 7,270,128 B2 | 9/2007 | Berthon-Jones et al. |
| 7,296,573 B2 | 11/2007 | Estes et al. |
| 7,322,937 B2 | 1/2008 | Blomberg et al. |
| D561,330 S | 2/2008 | Richards et al. |
| 7,338,410 B2 | 3/2008 | Dardik |
| 7,341,057 B2 | 3/2008 | Scarrott et al. |
| 7,341,059 B2 | 3/2008 | Moody et al. |
| 7,347,203 B2 | 3/2008 | Marler et al. |
| D566,833 S | 4/2008 | Richards et al. |
| 7,353,824 B1 | 4/2008 | Forsyth et al. |
| 7,360,537 B2 | 4/2008 | Snyder et al. |
| RE40,402 E | 6/2008 | Leonhardt et al. |
| 7,390,305 B2 | 6/2008 | Nuttall |
| 7,406,966 B2 | 8/2008 | Wondka |
| 7,419,670 B2 | 9/2008 | Zhong et al. |
| 7,422,014 B1 | 9/2008 | Smith |
| 7,431,031 B2 | 10/2008 | Hete et al. |
| 7,448,381 B2 | 11/2008 | Sasaki et al. |
| 7,448,383 B2 | 11/2008 | Delache et al. |
| 7,469,700 B2 | 12/2008 | Baran |
| 7,472,702 B2 | 1/2009 | Beck et al. |
| 7,472,705 B2 | 1/2009 | Baran |
| 7,478,635 B2 | 1/2009 | Wixey et al. |
| 8,066,001 B2 * | 11/2011 | Cegla ............... 128/200.24 |
| 2001/0004893 A1 | 6/2001 | Biondi et al. |
| 2001/0004894 A1 | 6/2001 | Bourdon |
| 2001/0039951 A1 | 11/2001 | Strickland, Jr. |
| 2001/0047805 A1 | 12/2001 | Scarberry et al. |
| 2002/0000228 A1 | 1/2002 | Schoeb |
| 2002/0005195 A1 * | 1/2002 | Shick et al. ............ 128/200.14 |
| 2002/0005197 A1 | 1/2002 | DeVires et al. |
| 2002/0007831 A1 | 1/2002 | Davenport et al. |
| 2002/0023645 A1 | 2/2002 | Zdrojkowski et al. |
| 2002/0026935 A1 | 3/2002 | Schmidt et al. |
| 2002/0026940 A1 | 3/2002 | Brooker et al. |
| 2002/0029779 A1 | 3/2002 | Schmidt et al. |
| 2002/0073993 A1 | 6/2002 | Weinstein et al. |
| 2002/0082512 A1 | 6/2002 | Strom |
| 2002/0088465 A1 | 7/2002 | Hill |
| 2002/0096173 A1 | 7/2002 | Berthon-Jones et al. |
| 2002/0115533 A1 | 8/2002 | Horstel et al. |
| 2002/0121278 A1 | 9/2002 | Hete et al. |
| 2002/0134704 A1 | 9/2002 | Mitchell et al. |
| 2002/0172645 A1 | 11/2002 | Conner |
| 2003/0000528 A1 | 1/2003 | Eklund et al. |
| 2003/0056788 A1 | 3/2003 | Faithfull et al. |
| 2003/0062045 A1 | 4/2003 | Woodring et al. |
| 2003/0066528 A1 | 4/2003 | Hill et al. |
| 2003/0121519 A1 | 7/2003 | Estes et al. |
| 2003/0127092 A1 * | 7/2003 | Pelerossi et al. ......... 128/200.24 |
| 2003/0140925 A1 | 7/2003 | Sapienza et al. |
| 2003/0145856 A1 | 8/2003 | Zdrojkowski et al. |
| 2003/0205229 A1 | 11/2003 | Crockford et al. |
| 2003/0205230 A1 | 11/2003 | Shusterman et al. |
| 2003/0213488 A1 | 11/2003 | Remmers et al. |
| 2003/0213491 A1 | 11/2003 | Berthon-Jones et al. |
| 2003/0221689 A1 | 12/2003 | Berthon-Jones |
| 2003/0226562 A1 | 12/2003 | Schmidt et al. |
| 2003/0230307 A1 | 12/2003 | DeVries et al. |
| 2003/0234017 A1 | 12/2003 | Pelerossi et al. |
| 2004/0000310 A1 | 1/2004 | Wickham et al. |
| 2004/0025870 A1 | 2/2004 | Harrison et al. |
| 2004/0033200 A1 | 2/2004 | Ezban et al. |
| 2004/0035417 A1 | 2/2004 | Ottolangui |
| 2004/0040557 A1 | 3/2004 | Salter et al. |
| 2004/0063544 A1 | 4/2004 | Lawson |
| 2004/0074494 A1 | 4/2004 | Frater |
| 2004/0084049 A1 | 5/2004 | Baran |
| 2004/0084050 A1 | 5/2004 | Baran |
| 2004/0097821 A1 | 5/2004 | Blomberg et al. |
| 2004/0097850 A1 | 5/2004 | Plante |
| 2004/0100477 A1 | 5/2004 | Morita et al. |
| 2004/0103896 A1 | 6/2004 | Jafari et al. |
| 2004/0112382 A1 | 6/2004 | Schneider et al. |
| 2004/0133123 A1 | 7/2004 | Leonhardt et al. |
| 2004/0134492 A1 | 7/2004 | Dardik |
| 2004/0156917 A1 | 8/2004 | Conner |
| 2004/0158178 A1 | 8/2004 | Fowler-Hawkins |
| 2004/0173209 A1 | 9/2004 | Grychowski et al. |
| 2004/0200477 A1 | 10/2004 | Bleys et al. |
| 2004/0211422 A1 | 10/2004 | Arcilla et al. |
| 2004/0221848 A1 | 11/2004 | Hill |
| 2004/0221851 A1 | 11/2004 | Madsen |
| 2004/0221854 A1 | 11/2004 | Hete et al. |
| 2004/0226562 A1 | 11/2004 | Bordewick |
| 2004/0255943 A1 | 12/2004 | Morris et al. |
| 2005/0005935 A1 | 1/2005 | Gradon |
| 2005/0005936 A1 | 1/2005 | Wondka |
| 2005/0005937 A1 | 1/2005 | Farrugia et al. |
| 2005/0005938 A1 | 1/2005 | Berthon-Jones et al. |
| 2005/0016536 A1 | 1/2005 | Rapoport et al. |
| 2005/0034727 A1 | 2/2005 | Shusterman et al. |
| 2005/0038353 A1 | 2/2005 | Rapoport et al. |
| 2005/0039746 A1 | 2/2005 | Grychowski et al. |
| 2005/0061321 A1 | 3/2005 | Jones |
| 2005/0076910 A1 | 4/2005 | Berthon-Jones et al. |

(56) References Cited

U.S. PATENT DOCUMENTS

| | | |
|---|---|---|
| 2005/0081859 A1 | 4/2005 | Scarberry et al. |
| 2005/0087187 A1 | 4/2005 | Berthon-Jones et al. |
| 2005/0087190 A1 | 4/2005 | Jafari et al. |
| 2005/0092321 A1 | 5/2005 | Aylsworth et al. |
| 2005/0098175 A1 | 5/2005 | Stradella |
| 2005/0098176 A1 | 5/2005 | Hoffrichter |
| 2005/0098179 A1 | 5/2005 | Burton et al. |
| 2005/0109340 A1 | 5/2005 | Tehrani |
| 2005/0125002 A1 | 6/2005 | Baran et al. |
| 2005/0126573 A1 | 6/2005 | Jaffre et al. |
| 2005/0139212 A1 | 6/2005 | Bourdon |
| 2005/0165334 A1 | 7/2005 | Lurie |
| 2005/0166920 A1 | 8/2005 | Delache et al. |
| 2005/0172960 A1 | 8/2005 | Gutsell et al. |
| 2005/0176761 A1 | 8/2005 | Pregel et al. |
| 2005/0188991 A1 | 9/2005 | Sun et al. |
| 2005/0203008 A1 | 9/2005 | Johansson et al. |
| 2005/0205085 A1 | 9/2005 | Blacker et al. |
| 2005/0205512 A1 | 9/2005 | Scarrott et al. |
| 2005/0211248 A1 | 9/2005 | Lauk et al. |
| 2005/0211249 A1 | 9/2005 | Wagner et al. |
| 2005/0224078 A1 | 10/2005 | Zdrojkowski et al. |
| 2005/0229931 A1 | 10/2005 | Denyer et al. |
| 2005/0235985 A1 | 10/2005 | Niles et al. |
| 2005/0235993 A1 | 10/2005 | Baecke et al. |
| 2005/0241639 A1 | 11/2005 | Zilberg |
| 2005/0247313 A1 | 11/2005 | Niles et al. |
| 2005/0247315 A1 | 11/2005 | Estes et al. |
| 2005/0268912 A1 | 12/2005 | Norman et al. |
| 2005/0268913 A1 | 12/2005 | Morris et al. |
| 2005/0274379 A1 | 12/2005 | Bruce et al. |
| 2005/0274381 A1 | 12/2005 | Deane et al. |
| 2005/0283089 A1 | 12/2005 | Sullivan et al. |
| 2005/0284476 A1 | 12/2005 | Blanch et al. |
| 2006/0002887 A1 | 1/2006 | Fitzpatrick et al. |
| 2006/0002888 A1 | 1/2006 | Fitzpatrick et al. |
| 2006/0002889 A1 | 1/2006 | Fitzpatrick |
| 2006/0005834 A1 | 1/2006 | Aylsworth et al. |
| 2006/0011195 A1 | 1/2006 | Zarychta |
| 2006/0011197 A1 | 1/2006 | Hodson |
| 2006/0011200 A1 | 1/2006 | Remmers et al. |
| 2006/0021618 A1 | 2/2006 | Berthon-Jones et al. |
| 2006/0032503 A1 | 2/2006 | Berthon-Jones et al. |
| 2006/0070625 A1 | 4/2006 | Ayappa et al. |
| 2006/0079799 A1 | 4/2006 | Green et al. |
| 2006/0086358 A1 | 4/2006 | Kushnir et al. |
| 2006/0090753 A1 | 5/2006 | Pelerossi et al. |
| 2006/0096594 A1 | 5/2006 | Bonney et al. |
| 2006/0102182 A1 | 5/2006 | Scarrott et al. |
| 2006/0107953 A1 | 5/2006 | Truschel et al. |
| 2006/0130835 A1 | 6/2006 | Truschel et al. |
| 2006/0144398 A1 | 7/2006 | Doshi et al. |
| 2006/0157052 A1 | 7/2006 | Foley et al. |
| 2006/0169281 A1 | 8/2006 | Aylsworth et al. |
| 2006/0178245 A1 | 8/2006 | Schiller et al. |
| 2006/0180150 A1 | 8/2006 | Dittmann |
| 2006/0185673 A1 | 8/2006 | Critzer et al. |
| 2006/0196507 A1 | 9/2006 | Bradley |
| 2006/0196508 A1 | 9/2006 | Chalvignac |
| 2006/0201500 A1 | 9/2006 | Von Hollen et al. |
| 2006/0201502 A1 | 9/2006 | Lieberman et al. |
| 2006/0201505 A1 | 9/2006 | Remmers et al. |
| 2006/0201508 A1 | 9/2006 | Forsyth et al. |
| 2006/0201509 A1 | 9/2006 | Forsyth et al. |
| 2006/0213507 A1 | 9/2006 | Foley et al. |
| 2006/0213518 A1 | 9/2006 | DeVries |
| 2006/0217627 A1 | 9/2006 | Nuttall |
| 2006/0223675 A1 | 10/2006 | Lew |
| 2006/0237014 A1 | 10/2006 | Makinson et al. |
| 2006/0243274 A1 | 11/2006 | Lieberman et al. |
| 2006/0249153 A1 | 11/2006 | DeVries et al. |
| 2006/0249155 A1 | 11/2006 | Gambone |
| 2006/0272642 A1 | 12/2006 | Chalvignac |
| 2007/0000494 A1 | 1/2007 | Banner et al. |
| 2007/0017518 A1 | 1/2007 | Farrugia et al. |
| 2007/0023036 A1 | 2/2007 | Grychowski et al. |
| 2007/0032732 A1 | 2/2007 | Shelley et al. |
| 2007/0044796 A1 | 3/2007 | Zdrojkowski et al. |
| 2007/0056502 A1 | 3/2007 | Lu |
| 2007/0078086 A1 | 4/2007 | Axelsen et al. |
| 2007/0078087 A1 | 4/2007 | Axelsen et al. |
| 2007/0084467 A1 | 4/2007 | Scarrott |
| 2007/0089740 A1 | 4/2007 | Baumert et al. |
| 2007/0107719 A1 | 5/2007 | Blacker et al. |
| 2007/0151563 A1 | 7/2007 | Ozaki et al. |
| 2007/0175474 A1 | 8/2007 | Scarrott et al. |
| 2007/0185052 A1 | 8/2007 | Yedgar et al. |
| 2007/0193581 A1 | 8/2007 | Laurila et al. |
| 2007/0199566 A1 | 8/2007 | Beeri |
| 2007/0204864 A1 | 9/2007 | Grychowski et al. |
| 2007/0225685 A1 | 9/2007 | Plante |
| 2007/0235028 A1 | 10/2007 | Bruce et al. |
| 2007/0256690 A1 | 11/2007 | Faram |
| 2007/0277823 A1 | 12/2007 | Al-Ali et al. |
| 2007/0283958 A1 | 12/2007 | Naghavi |
| 2008/0000475 A1 | 1/2008 | Hill |
| 2008/0000477 A1 | 1/2008 | Huster et al. |
| 2008/0000478 A1 | 1/2008 | Matthiessen et al. |
| 2008/0000479 A1 | 1/2008 | Elaz et al. |
| 2008/0011301 A1 | 1/2008 | Qian |
| 2008/0015456 A1 | 1/2008 | McCawley et al. |
| 2008/0021355 A1 | 1/2008 | Huster et al. |
| 2008/0029085 A1 | 2/2008 | Lawrence et al. |
| 2008/0029096 A1 | 2/2008 | Kollmeyer et al. |
| 2008/0043443 A1 | 2/2008 | Nagao et al. |
| 2008/0053438 A1 | 3/2008 | DeVries et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0053456 A1 | 3/2008 | Brown et al. |
| 2008/0060646 A1 | 3/2008 | Isaza |
| 2008/0060647 A1 | 3/2008 | Messenger et al. |
| 2008/0060656 A1 | 3/2008 | Isaza |
| 2008/0078383 A1 | 4/2008 | Richards et al. |
| 2008/0083407 A1 | 4/2008 | Grychowski et al. |
| 2008/0091117 A1 | 4/2008 | Choncholas et al. |
| 2008/0092894 A1 | 4/2008 | Nicolazzi et al. |
| 2008/0096728 A1 | 4/2008 | Foley et al. |
| 2008/0108905 A1 | 5/2008 | Lurie |
| 2008/0110451 A1 | 5/2008 | Dunsmore et al. |
| 2008/0110455 A1 | 5/2008 | Dunsmore et al. |
| 2008/0110461 A1 | 5/2008 | Mulqueeny et al. |
| 2008/0115786 A1 | 5/2008 | Sinderby et al. |
| 2008/0135735 A1 | 6/2008 | Gottesman et al. |
| 2008/0142004 A1 | 6/2008 | Wasnick |
| 2008/0142011 A1 | 6/2008 | Aylsworth et al. |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0190428 A1 | 8/2008 | Yu |
| 2008/0190429 A1 | 8/2008 | Tatarek |
| 2008/0196724 A1 | 8/2008 | Nadjafizadeh et al. |
| 2008/0200775 A1 | 8/2008 | Lynn |
| 2008/0200819 A1 | 8/2008 | Lynn et al. |
| 2008/0202528 A1 | 8/2008 | Carter et al. |
| 2008/0214357 A1 | 9/2008 | Farinelli et al. |
| 2008/0216830 A1 | 9/2008 | Richards et al. |
| 2008/0216834 A1 | 9/2008 | Easley et al. |
| 2008/0223361 A1 | 9/2008 | Nieuwstad |
| 2008/0236582 A1 | 10/2008 | Tehrani |
| 2008/0257345 A1 | 10/2008 | Snyder et al. |
| 2008/0257349 A1 | 10/2008 | Hedner et al. |
| 2008/0264412 A1 | 10/2008 | Meyer et al. |
| 2008/0264419 A1 | 10/2008 | Lomask et al. |
| 2008/0283060 A1 | 11/2008 | Bassin |
| 2008/0283062 A1 | 11/2008 | Esposito, Jr. |
| 2008/0295839 A1 | 12/2008 | Habashi |
| 2008/0295840 A1 | 12/2008 | Glaw |
| 2008/0302364 A1 | 12/2008 | Garde et al. |
| 2008/0308104 A1 | 12/2008 | Blomberg et al. |
| 2009/0007915 A1 | 1/2009 | Brunner et al. |

(56) References Cited

U.S. PATENT DOCUMENTS

2009/0007916 A1 1/2009 Ralfs
2010/0101573 A1 4/2010 Foley et al.
2012/0097164 A1 4/2012 Rozario et al.

FOREIGN PATENT DOCUMENTS

EP           2 444 114 A1   4/2012
WO    WO 2008/063966 A1   5/2008

OTHER PUBLICATIONS

"Flutter® Mucus Clearance Device", Axcan Scandipharm, Inc., 2003, (11 pages).
Acapella duet, Vibratory PEP Therapy System with Medicated Aerosol Nebulizer, Smiths Medical ADS, Inc. (2 pages).
"Quake® Vibratory PEP Device" Thayer Medical Corp., (5 pages).
"Introduction to Powerlung for Healthcare Professionals," Powerlung Incorporated, 2004, (10 pages).
European Search Report for EP 13 15 7675, dated Jun. 24, 2013.

* cited by examiner

RESPIRATORY THERAPY DEVICE HAVING STANDARD AND OSCILLATORY PEP WITH NEBULIZER

BACKGROUND

The present disclosure relates to respiratory therapy devices. More particularly, the present disclosure relates to hand-held respiratory therapy devices used for positive expiratory pressure (PEP) therapy.

Hand-held devices used for PEP therapy are known. One known example is the ACAPELLA® Vibratory PEP Therapy System device marketed by Smiths Industries ASD, Inc. See U.S. Pat. Nos. 7,699,054; 7,059,324; 6,776,159; and 6,581,598 and U.S. Patent Application Publication No. 2008/0078383. Examples of standard or non-oscillatory PEP therapy devices are shown, for example, in U.S. Pat. Nos. 6,848,443; 6,557,549; 6,083,141; 5,910,071; and 5,890,998. Patients desiring both oscillatory (or vibratory) PEP therapy and standard PEP therapy, therefore, need to have access to both types of devices. Some of the prior art PEP therapy devices include a port for coupling to a nebulizer container. However, during patient exhalation, the nebulized medication is lost to the atmosphere in some prior art devices.

What is needed, therefore, is a single device that has the capability of both standard and oscillatory PEP therapy and that, optionally, includes a nebulizer container connector that inhibits or minimizes the loss of nebulized medication to the atmosphere during patient exhalation. Such a device should be easy to use and packaged in a fairly compact manner so as to be hand-held.

SUMMARY

The present invention may comprise one or more of the features recited in the appended claims and/or the following features which each are considered to be optional and which, alone or in any combination, may comprise patentable subject matter:

A respiratory therapy device may include a housing which may have a first port to receive a person's exhaled breath, a second port, and a third port. A standard positive expiratory pressure (PEP) device may be coupled to the second port. An oscillatory PEP device may be coupled to the third port. A manually operable valve member may be movable between a first position blocking the third port and allowing the person's exhaled breath to flow to the standard PEP device through the second port and a second position blocking the second port and allowing the person's exhaled breath to flow to the oscillatory PEP device through the third port.

In some embodiments, the standard PEP device may include a tube, a knob, and a cylindrical stem extending from the knob. The cylindrical stem may have a hollow central passage, an open end, and a plurality of apertures communicating with the hollow central passage. The stem may be situated adjacent the tube and may be movable to select how many of the plurality of apertures of the cylindrical stem are exposed to an interior region of the tube thereby to change a flow resistance of the standard PEP device.

The standard PEP device may further include a stem receiver at an end of the tube. The stem may be received in the stem receiver for rotation. The knob may be situated adjacent one end of the stem receiver and an opposite end of the stem receiver may be open. The tube of the standard PEP device may have a first segment and a second segment that may be perpendicular to the first segment.

In some embodiments, an adjuster may be coupled to the knob. The adjuster may engage a member of the oscillatory PEP device to adjust a characteristic of oscillation of the oscillatory PEP device, such as frequency or amplitude. The adjuster may include, for example, an eccentric disk having an edge that engages the member of the oscillatory PEP device. The member may have a rounded end and the edge of the eccentric disk may have a plurality of notches. The rounded end may index from notch to notch as the knob is rotated.

In some embodiments, the standard PEP device may include a tube having a tube wall that may define an interior region and that may have a plurality of apertures extending through the tube wall. The standard PEP device may further include a knob and a stem that may extend from the knob into the interior region defined by the tube wall. The knob may be rotatable by the knob to select how many of the plurality of apertures are blocked by the stem.

The oscillatory PEP device may include a flexible tube having a first end coupled to the third port. The flexible tube may have an opening near a second end. The oscillatory PEP device may include a stopper that may be movable to change a frequency at which the flexible tube may oscillates when the person's exhaled breath passes through the flexible tube and exits the opening.

According to this disclosure, the stopper may include a flexible stick that may be flexed by varying amounts to change the amount by which the flexible tube is able to flex in at least a first direction. The person's exhaled breath may exit the opening in the flexible tube toward the flexible stick. The flexible stick may be longer than the flexible tube in some embodiments. The oscillatory PEP device may include a member coupled to the flexible stick. The member may engage an adjustment device of the standard PEP device so that the same adjustment device may be used to adjust operation of the standard PEP device and the oscillatory PEP device. The adjustment device may include a rotatable knob, for example.

Also according to this disclosure, the stopper may include a fulcrum that may be moved along a length of the flexible tube. The flexible tube may be coupled to the third port by a substantially rigid tube and the stopper may include a collar that may be slidable along the substantially rigid tube. The stopper may include a connector that may interconnect the collar and fulcrum so that movement of the collar along the substantially rigid tube may move the fulcrum along the flexible tube. In some embodiments, the fulcrum may be cylindrical in shape.

In some embodiments, the housing has a fourth port and the respiratory therapy device may further have a nebulizer connector that may be coupled to the fourth port. The nebulizer connector may have a first one-way valve that may be located adjacent the fourth port. The first one-way valve normally may be closed and may open when the person inhales through the first port. The nebulizer connector may have a second one-way valve that may be spaced from the first one-way valve. The second one-way valve normally may be closed and may open when the person inhales to permit ambient air to enter into an interior region of the nebulizer connector. Thus, the first and second one-way valves may inhibit or minimize losses of nebulized medication during a patient's exhalation.

In some embodiments, the first one-way valve and the second one-way valve may be aligned with the third port. The first and second one-way valves may comprise umbrella valves, for example. The nebulizer connector may include a nebulizer port that may be situated between the first and second one-way valves. The nebulizer port may be adapted for coupling to a nebulizer. In some embodiments, the nebulizer connector may include a first tubular member that may carry the first one-way valve at a first end and that may carry the second one-way valve at a second end. The nebulizer connector may include a second tubular member that may be perpendicular to the first tubular member. The second tubular member may serve as the nebulizer port.

According to this disclosure, a respiratory therapy device may include a housing having a first port to receive a person's exhaled breath generally along a flow path. The housing may have an end wall that is spaced from the first port and that may be arranged generally perpendicular to the flow path. The end wall may have a second port, a third port, and a fourth port. A standard positive expiratory pressure (PEP) device may be coupled to the second port. An oscillatory PEP device may be coupled to the third port. A nebulizer connector may be coupled to the fourth port.

The respiratory therapy device may further include a first manually operable member that may be movable to select whether the first port communicates with the standard PEP device through the second port or whether the first port communicates with the oscillatory PEP device through the third port. Furthermore, a second manually operable member may be movable to adjust operation of at least one of the standard PEP device and the oscillatory PEP device. The second manually operable member may include a rotatable knob that, in turn, may have a first portion which adjusts operation of the standard PEP device when the knob is rotated and a second portion which adjusts operation of the oscillatory PEP device when the knob is rotated.

The first portion of the rotatable knob may include a cylindrical stem that may have a hollow core and a plurality of apertures extending through the cylindrical stem. The second portion of the rotatable knob may include a disk. The disk may be eccentric to an axis about which the knob rotates. In some embodiments, the disk may include an edge having notches that may selectively receive an adjustment member of the oscillatory PEP device when the respective notch is aligned with the adjustment member. The oscillatory PEP device may include a flexible tube and movement of the adjustment member by the disk may change a characteristic of oscillation of the flexible tube. For example, the characteristic of oscillation changed by movement of the disk may include at least one of a frequency of oscillation and an amplitude of oscillation. According to this disclosure, the oscillatory PEP device may include an elongated stick coupled to the adjustment device and extending alongside the flexible tube. The adjustment device may be formed as a tab extending from the elongated stick.

According to this disclosure, the first manually operable member may include a knob, a stem extending from the knob, and a plug coupled to the stem. The plug may have a first end that may block the second port from communicating with the first port when the knob is rotated to a first position and the plug may have a second end that may block the third port from communicating with the first port when the knob is rotated to a second position. In some embodiments, the first and second ends of the plug are tapered. For example, the first and second ends of the plug may be substantially conical.

In some embodiments, the knob may rotate through about 180 degrees when moving between the first and second positions. The knob and stem may rotate about a first axis and the plug may be shaped to define a second axis that may extend between the first and second ends. The second axis may be orthogonal to the first axis. The plug may be coupled to the stem by a tab that positions the plug in offset relation with the stem. In alternative embodiments, the plug may be coupled directly to the stem.

According to this disclosure, the end wall may be circular and the housing may further include a cylindrical wall that may extend from the end wall toward the first port and that may define a chamber adjacent the second, third, and fourth ports. The first manually operable member may include a knob that may be situated outside the chamber, a stem that may extend from the knob into the chamber through the cylindrical wall, and a plug that may be situated inside the chamber.

In some embodiments, the nebulizer connector may include a T-shaped connector that may have a first tubular segment with a first end that may connect to the fourth port and a second end spaced from the first end. The T-shaped connector may have a second tubular segment that may extend from the first segment in perpendicular relation therewith. The second segment may have an open end sized to couple to a nebulizer container.

According to this disclosure, at least one of the first and second ends of the first segment of the T-shaped connector may carry a one-way valve. For example, both of the first and second ends of the first segment of the T-shaped connector may carry a one-way valve. Each of the one-way valves may comprise an umbrella valve, for example. The one-way valve may be normally closed and may open in response to a person's inhalation through the first port.

According to an aspect of this disclosure, a respiratory therapy device may include a housing that may have a first port to receive a person's exhaled breath and that may have an interior region. A standard positive expiratory pressure (PEP) device may be coupled to the housing and may have a first passage that selectively communicates with the interior region of the housing. An oscillatory PEP device may be coupled to the housing and may have a second passage that selectively communicates with the interior region of the housing. At least one selector may be movable to select whether the standard PEP device or the oscillatory PEP device is in communication with the interior region of the housing. At least one adjuster may be movable to adjust the operation of at least one of the standard PEP device and the oscillatory PEP device.

The at least one adjuster may include, for example, a single knob that may be rotatable to adjust the operation of both the standard PEP device and the oscillatory PEP device. The at least one adjuster may include a pair of second adjusters, a first of which may adjust operation of the standard PEP device and a second of which may adjust operation of the oscillatory PEP device. The respiratory therapy device may further include a nebulizer connector that may be coupled to the housing and that may have a first one-way valve which normally may be closed and which may open when a person inhales through the first port.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

A respiratory therapy device 20 includes a standard positive expiratory pressure (PEP) therapy device 100 and an oscillatory PEP therapy device 200 as shown in FIGS. 1-4. A user is able to select whether to use device 100 or device 200 as will be described in further detail below. Optionally, a nebulizer connector 300 is included in device 20 as shown in the illustrative embodiment.

Figure 1:
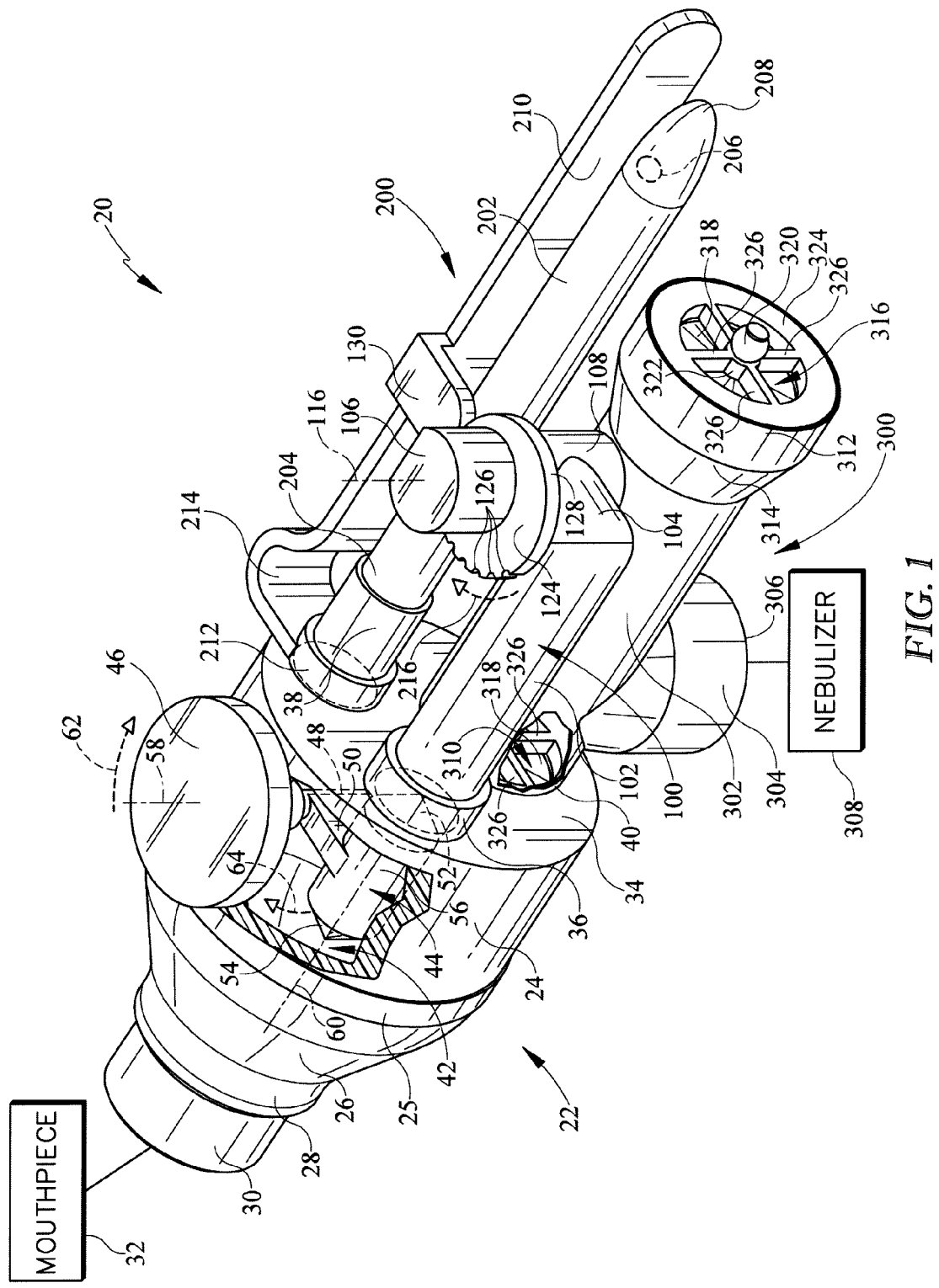
FIG. 1 is a perspective view of a respiratory therapy device showing a housing, a diagrammatic mouthpiece coupleable to a first port of the housing, a standard PEP device coupled to a second port of the housing, an oscillatory PEP device coupled to a third port of the housing, the oscillatory PEP device being longer than the standard PEP device, a nebulizer connector coupled to a fourth port of the housing, a diagrammatic nebulizer coupleable to the nebulizer connector, a first knob extending upwardly from the housing and having a plug positioned in a chamber of the housing to block communication between the first port and the second port, and a second knob mounted to a distal end of the standard PEP device and having a notched disk engaging an adjustment member of the oscillatory PEP device.

Device 20 includes a housing 22 having a generally cylindrical main body 24, a somewhat frustoconical transition portion 26, a generally cylindrical shoulder portion 28, and a generally cylindrical first port 30 as shown in FIG. 1. First port 30 is sized and configured to couple to a mouthpiece 32, shown diagrammatically in FIG. 1. Mouthpiece 32 is typically a disposable piece that is swapped out from person-to-person or after becoming sufficiently worn. In some embodiments, mouthpiece 32 includes a generally cylindrical portion that press fits over the outer surface of first port 30 until a proximal end of the mouth piece engages and end surface 29 (FIG. 2) of shoulder portion 28. In other embodiments, mouthpiece 32 includes a generally cylindrical portion that press fits into an inner surface of port 30. Mouthpiece 32 also typically includes a flattened portion that is configured for receipt within a users mouth.

Housing 22 has a generally circular end wall 34 that includes second, third, and fourth ports 36, 38, 40 as shown in FIG. 1. It should be understood that housing 22 is a generally hollow member or body that defines a main internal chamber 42 which is able to pneumatically communicate with each of ports 30, 36, 38, 40. However, device 20 has a manually operable valve member 44 that is movable between a first position blocking second port 36 from pneumatically communicating with chamber 42, and therefore with port 30, and a second position blocking third port 38 from pneumatically communicating with chamber 42, and therefore with port 30. For ease of manufacturing, in some embodiments, portion 24 of housing 22 is formed separately from portions 26, 28, 30 such that housing 22 is a two-piece housing. In the illustrative example, an annular coupling collar 25 extends from portion 26 and portion 24 is fastened to collar 25 such as via one or more of radio frequency (RF) welding, a suitable adhesive, or a threaded connection, for example.

Figure 2:
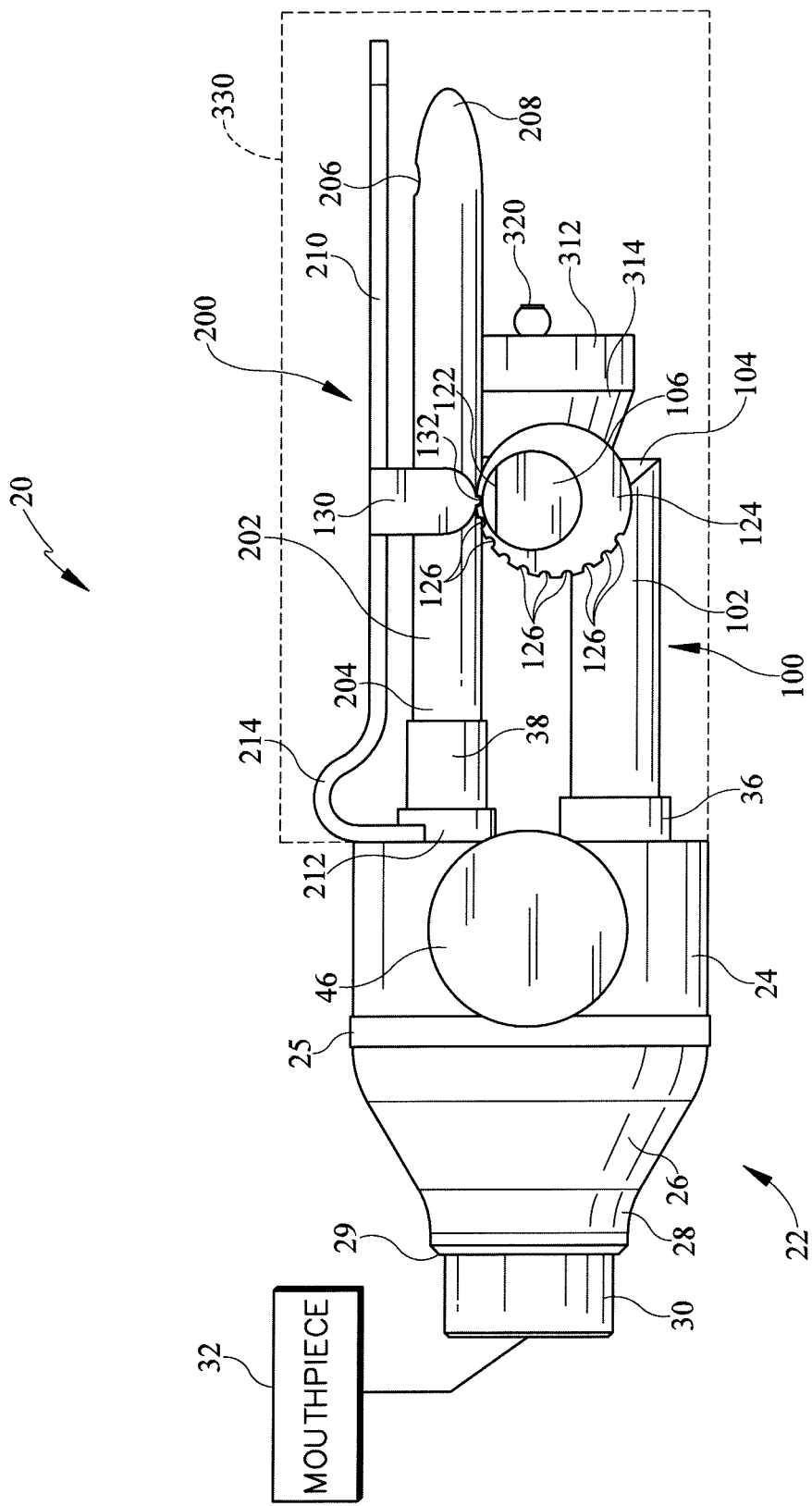
FIG. 2 is a top view of the respiratory therapy device of FIG. 1 showing the adjustment member of the oscillatory PEP device having a tip received in a first notch of the notched disk of the second knob, the adjustment member extending from a stick that extends alongside a flexible tube of the oscillatory PEP device, and a diagrammatic cover (in phantom) coupled to the housing and covering the standard and oscillatory PEP devices.

Standard PEP device 100 is coupled to second port 36 and oscillatory PEP device 200 is coupled to third port 38 as shown, for example, in FIGS. 1 and 2. Nebulizer connector 300 of the illustrative device 20 is coupled to fourth port 40. In other embodiments, port 40 and nebulizer connector 300 are omitted. In some such embodiments, circular wall 34 fills in the space defined by port 40. In such embodiments, a user exhales through device 20 and then removes device 20 from his or her mouth to inhale. In other embodiments omitting nebulizer connector 300, port 40 is still present to provide a large orifice to allow inspiratory air to move into chamber 42 and then through port 30 as a user inhales. As will be described in further detail below, a one-way valve is provided adjacent port 40 to allow inspiratory air to flow into chamber 42 of housing 22 through port 40 and to block expiratory air from flowing out of chamber 42 through port 40.

In use, a patient or user exhales and inhales through mouthpiece 32. During exhalation, the patients expired breath is forced through chamber 42 of housing 22 and then through either the standard PEP device 100 or the oscillatory PEP device 200 depending upon the position of valve member 44.

Thus, if valve member 44 is in the first position blocking port 36, then the patient's exhaled breath is forced through port 38 and then through oscillatory PEP device 200. On the other hand, if valve member 44 is in the second position blocking port 38, then the patient's exhaled breath is forced through port 36 and then through standard PEP device 100.

A manually operable member, such as illustrative knob 46, is located above main portion 24 of housing 22 and is manually rotatable to move valve member 44 between the first and second positions. A stem 48 extends generally vertically downwardly from knob 46 and a tab 50 extends radially outwardly from the stem 48. Tab 50 interconnects stem 48 and valve member 44 as shown in FIG. 1. Thus, tab 50 positions valve member 44 in offset relation with stem 48. In the illustrative embodiment, valve member 44 has a tapered or generally conical first end 52 and a tapered or generally conical second end 54 as also shown in FIG. 1. Valve member 44 also has a cylindrical main portion 56 extending between ends 52, 54. When valve member 44 is in the first position, end 52 plugs or closes port 36 and when valve member 44 is in the second position, end 54 plugs or closes port 38. Thus, valve member 44 is sometimes referred to herein as plug 44.

While ends 52, 54 are tapered or conical in the illustrative example, it is within the scope of this disclosure for ends 52, 54 of plug 44 to have other shapes such as being somewhat rounded, hemispherical, or even flat. In some embodiments, a resilient member such as an o-ring may be provided on each of ends 52, 54 or on an inner surface of port 36 or on an inner surface of wall 34. Alternatively or additionally, a gasket or seal may be provided on the inner surface of port 36 or on the inner surface of wall 36. The purpose of such o-rings, seals or gaskets, if provided, is to enhance the pneumatic sealing between ends 52, 54 of plug 44 and ports 36, 38.

In the illustrative example, knob 46 and stem 48 rotate about a first axis 58 and plug 44 is shaped to define a second axis 60 extending between first and second ends 52, 54. The first and second axes 58, 60 are orthogonal in the illustrative example. Also in the illustrative example, knob 46 is rotated through about 180 degrees when moving the valve member 44 between the first and second positions. Thus, tab 50 is substantially parallel to wall 34 when valve member 44 is in each of the first and second positions and axis 60 of valve member 44 is substantially perpendicular with wall 34 when valve member 44 is in each of the first and second positions. Accordingly, the axis 58 about which knob 46 and stem 50 rotate is about equidistant from each of ports 36, 38. Stated another way, a plane passing through axis 58 and perpendicular to wall 34 will be located about midway between the centers of ports 36, 38.

In FIG. 1, valve member 44 is shown in the first position blocking port 36. To move valve member 44 to the second position, knob 46 is rotated about axis 58 in the direction of arrow 62 which causes valve member 44 to move within chamber 42 in the direction of arrow 64 as also shown in FIG. 1. Thus, housing 22 is sized and configured such that chamber 42 is sufficiently large to permit valve member 44 to swing therein through an arc of about 180 degrees. In some embodiments, a latch or lock (not shown) is provided to retain knob 46 and valve member 44 in the first and second positions. Such a latch or lock may comprise, for example, a detent mechanism such as a snap finger or spring loaded detent ball on housing 22 that is received a pair of pockets of knob 46 or stem 48 to retain knob 46 and plug 44 in either the first position or the second position, as the case may be.

Standard PEP device 100 includes an L-shaped tube which is made up of an elongated main tubular portion or segment 102 that has a first end coupled to port 36 and a short portion or segment 104 that extends from a second end of main portion 102 toward oscillatory PEP device 200 as shown in FIGS. 1 and 2. Housing 22 and tubular portions 102, 104 are made of a plastics material. As such, in some embodiments, the first end of portion 102 is coupled to port 36 via radio frequency (RF) welding. In other embodiments, the first end of portion 102 is coupled to port 36 with a suitable adhesive. In still other embodiments, the first end of tube 102 is press fit into port 36 to couple standard PEP device 100 to housing 22. In further embodiments, tubular portions 102, 104 are integrally molded with housing 22. In the illustrative example, port 36 is defined by a cylindrical wall extending in a cantilevered manner from wall 34 and tubular portion 102 is cylindrical. In other embodiments, the wall defining port 36 and the tubular portion 102 may have other cross-sectional shapes such as square, rectangular, hexagonal, elliptical, or octagonal, just to name a few possibilities.

Figure 5:
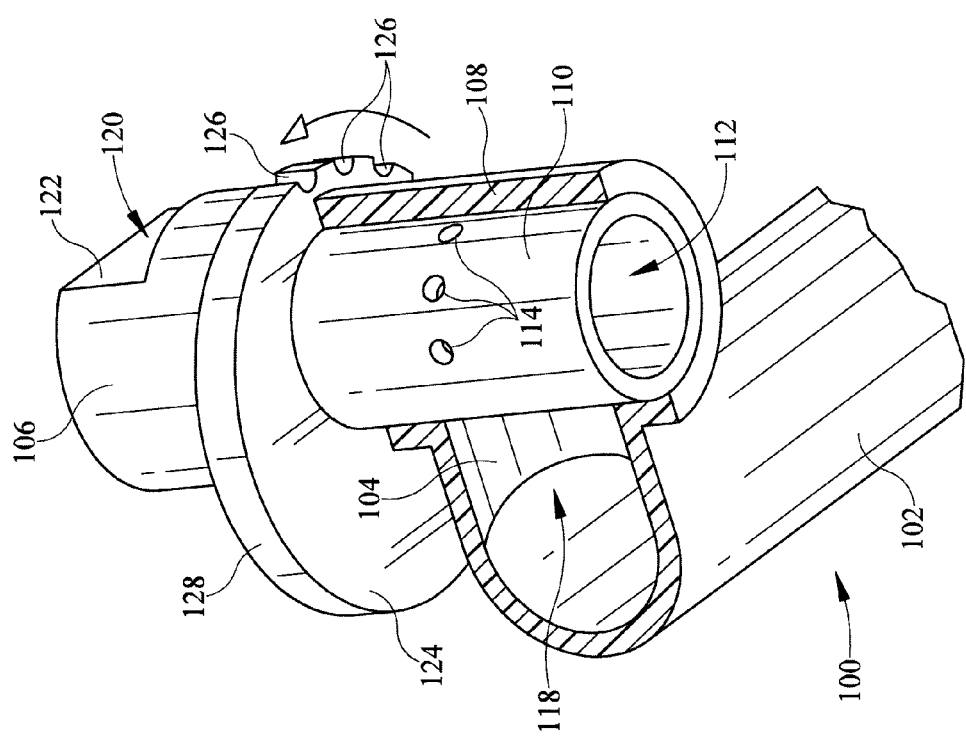
FIG. 5 is an enlarged perspective view, with portions broken away, of the distal end of the standard PEP device showing the second knob having a stem with a hollow core extending into a cylindrical stem receiver of the standard PEP device and showing a set of apertures that extend through the stem and that are movable to communicate with a tube of the standard PEP device.

Standard PEP device 100 further includes a manually operable member, such as illustrative knob 106, that is rotated to adjust the operation of standard PEP device 100. Device 100 includes a cylindrical stem receiver 108 situated at the end of tubular portion 104. Stem receiver 108 is integrally molded with portion 104 in the illustrative embodiment as shown in FIG. 5. Portions 102, 104 and stem receiver 108 are hollow and in pneumatic communication with each other and with port 36. Stem receiver 108 is open at its top and bottom. A cylindrical stem 110 extends downwardly from knob 106 and is received in stem receiver 108 as shown in FIG. 5. Stem 110 is a cylindrical tubular member with a bottom opening 112.

A plurality of small apertures 114 are formed radially through stem 110 as shown in FIG. 5. Knob 106 is rotatable about an axis 116, shown in FIG. 1, to change the number of apertures 114 that are in pneumatic communication with a pneumatic passage or interior region 118 of portion 104 of standard PEP device 100. The more apertures 114 that are in pneumatic communication with pneumatic passage 118 the less resistance there is to the user's exhalation. Conversely, the less apertures that are in communication with pneumatic passage 118, the more resistance there is to the user's exhalation.

Knob 106 has a cutout 120 which is defined in part by a flat surface 122 on the otherwise cylindrical body of knob 122. Cutout 120 enhances the ability of a user to grip and rotate knob 106 about axis 116. An adjuster 124 is situated between knob 106 and stem 110. In the illustrative example, adjuster 124 comprises an eccentric disk that includes a plurality of notches 126 formed in an edge 128 thereof. A member 130 of the oscillatory PEP device 200 has a detent 132 at a distal end thereof as shown in FIG. 2. Detent 132 indexes from notch 126 to notch 126 as knob 106 is rotated about axis 116. Receipt of detent 132 in any give notch 126 holds knob 106 in place and therefore, holds stem 110 in place within stem receiver 108. The number of apertures 114 in pneumatic communication with interior region or passage 118 is determined by which of notches 126 receives detent 132 which, in turn, corresponds to the rotational position of knob 116 about axis 116.

Oscillatory PEP device 200 includes a flexible tube 202 having a first end 204 coupled to third port 38 as shown in FIGS. 1 and 2. Flexible tube 202 is a somewhat torpedo or missile shaped hollow tube that when not in use extends in a straight, cantilevered manner from port 38 in parallel relation with main tubular portion 102 of standard PEP device 100. Flexible tube 202 has an opening 206 near a second end 208. Second end 208 is somewhat rounded. In use, a user's exhaled breath enters tube 202 through port 38 and moves generally longitudinally down the length of tube 202 and then exits opening 206 in a lateral direction or generally perpendicular to the longitudinal dimension of tube 202. As the exhaled air exits opening 206 of tube 202, tube 202 flexes back and forth in an oscillatory manner. In some embodiments, tube 202 is made of a rubber material, for example.

Oscillatory PEP device 200 includes a stopper 210 that is movable to change the oscillation characteristics of tube 202. Thus, by changing the position of stopper 210 relative to tube 202, an amplitude and/or frequency at which flexible tube 202 oscillates is changed. In the illustrative embodiment of device 20, stopper 210 comprises a flexible stick (sometimes referred to herein as stick 210) that is flexed by varying amounts to change the amount by which flexible tube 202 is able to flex in a first direction. Opening 206 is positioned such that the user's exhaled breath exits opening 206 and moves toward stick 210. In the illustrative embodiment, flexible stick 210 is longer than flexible tube 202 but this need not be the case.

Stopper 210 includes a collar 212 and an undulation or bulge 214 that interconnects collar 212 and the main, straight portion of stopper 210. Collar 212 is positioned around the outside of port 38 and tube 202 extends into port 38. A suitable fastening mechanism is provided in some embodiments to couple collar 214 and tube 202 to port 38. For example, in embodiments in which stick 210, collar 212, and undulation 214 are made from a plastics material, collar 212 is RF welded to port 38. Alternatively or additionally, a suitable adhesive is provided to couple collar 212 and tube 202 to port 38. Further alternatively or additionally, collar 212 is press fit over port 38 and tube 202 is press fit into port 38 in some embodiments.

As mentioned above, an eccentric disk 124 is coupled to knob 106 and receives a detent 132 at the end of member 130. Member 130 is formed integrally with stick 210 in the illustrative embodiment and projects therefrom toward knob 106. Thus, as the eccentric disk 124 rotates about axis 116 in the direction indicated by dotted arrow 216 in FIG. 1, eccentric disk 124 pushes on member 130 to flex stick 210 laterally outwardly away from flexible tube 202. The flexing of stick 210 occurs primarily at the undulation 214 such that the main portion of stick 210 remains generally straight regardless of the amount of flexing of stick 210 between minimum and maximum flexed positions. The receipt of detent 132 in any given notch 126 holds knob 106 in place having stick 210 flexed by a corresponding amount. Based on the preceding discussion, it will be appreciated that knob 106 serves as an adjustment device or adjuster for both the standard PEP device 100 and the oscillatory PEP device 200.

Figure 3:
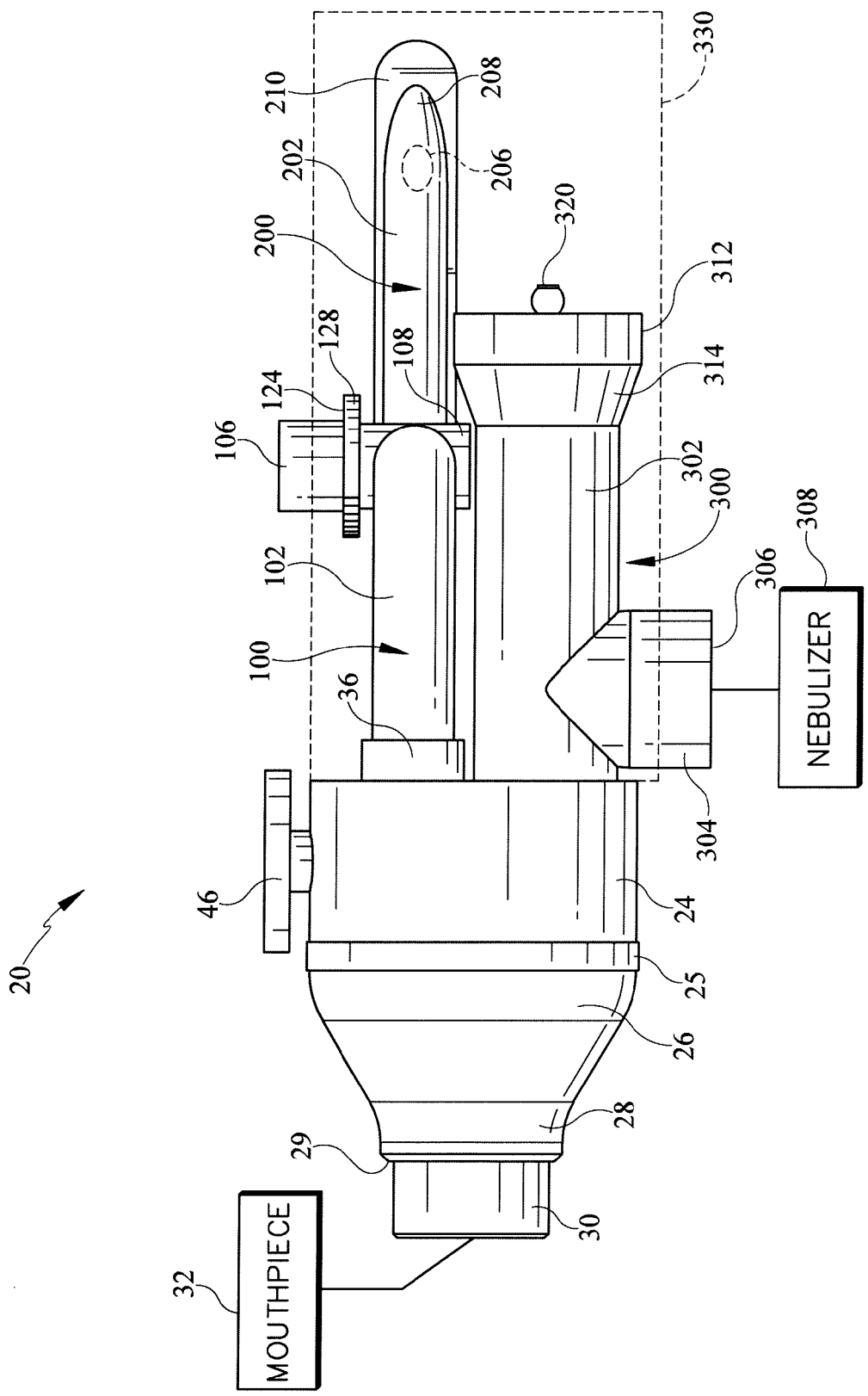
FIG. 3 is a side view of the respiratory therapy device of FIGS. 1 and 2 showing the first knob extending upwardly from the housing and showing the second knob extending upwardly above a top portion of the diagrammatic cover (in phantom)

Nebulizer connector 300 is coupled to fourth port 40 as mentioned previously. Connector 300 includes a main tubular portion 302 and a nebulizer attachment portion 304 as shown in FIGS. 1 and 3. Portion 304 extends downwardly from portion 302 such that portions 302, 304 form somewhat of a T-connector arrangement. In the illustrative example, portion 304 located along portion 302 closer to port 40 than to a distal end of portion 302.

Figure 4:
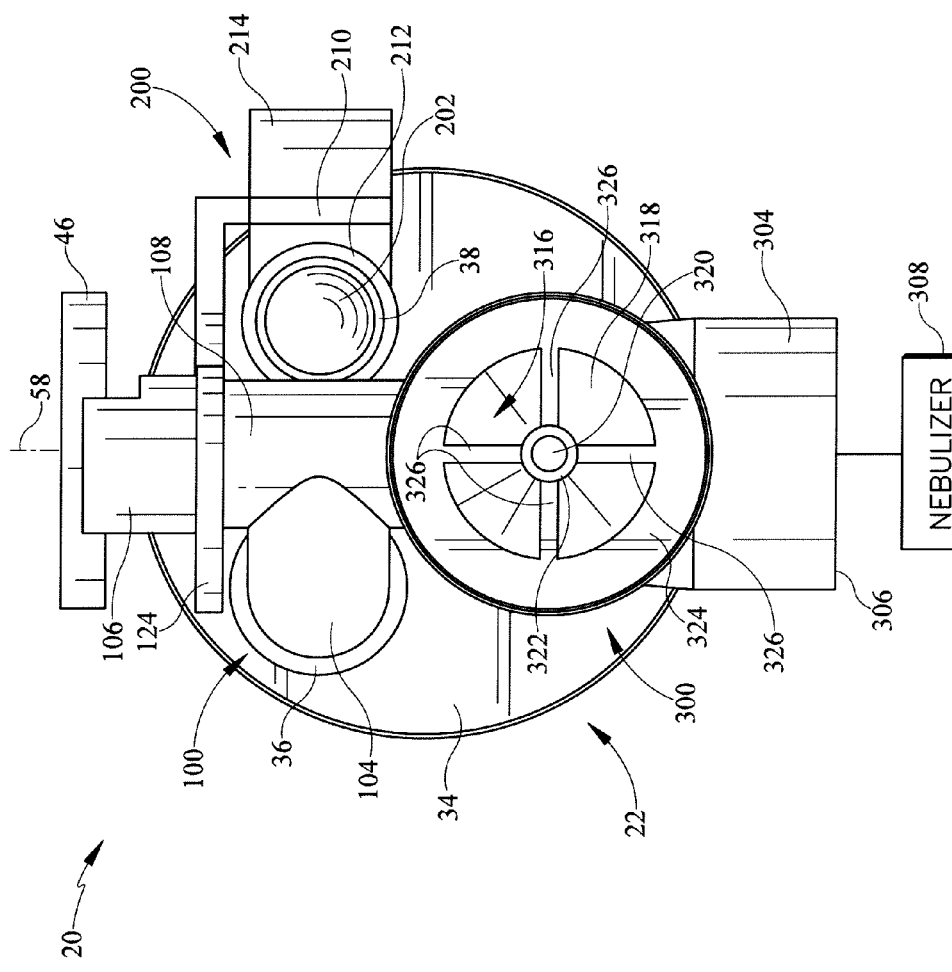
FIG. 4 is an end view of the respiratory therapy device of FIGS. 1-3 showing portions of a one-way valve exposed in a set of pie-shaped openings of a distal end of the nebulizer connector.

Portion 304 is hollow and is sized for connection to any number of nebulizer container styles. For example, portion 304 is threaded in some embodiments so that a nebulizer container with a threaded upper end is screwed onto portion 304. The thread or threads of portion 304 are located adjacent the open bottom end 306 of portion 304 and are internal to portion 304 in some embodiments and/or external to portion 304 in some embodiments. Alternatively, a suitable nebulizer container is press fit into or onto portion 304 if desired. That is, an upper end of an appropriately size nebulizer container is inserted into portion 304 with a press fit in some instances and, in other instances, an upper end of an appropriately sized nebulizer container receives bottom end 306 therein with a press fit. In FIGS. 1, 3 and 4, the diagrammatic block 308 which is labeled with the text "NEBULIZER" is intended to represent the nebulizer container that attaches to portion 304 of connector 300 and the pressure source that atomizes or nebulizes the liquid medication contained in the nebulizer container as is well known in the art.

A first one-way valve or check valve 310 is coupled to a proximal end of connector 300 and is located adjacent fourth port 40 as shown in FIG. 1. The first one-way valve 310 is normally closed forming a substantially air tight seal around port 40 but is configured to open in response to a user inhaling through first port 30 with sufficient force. Connector 300 includes an enlarged tubular end region 312 that interconnects with main tubular portion 302 via a frustoconical transition portion 314. Nebulizer connector 300 has a second check valve or one-way valve 316 which is spaced from the first one-way valve 310 and located at the distal end of connector 300.

The second one-way valve 316 is also normally closed and opens when the user inhales under certain conditions. In particular, second one-way valve 316 is more apt to open during a user's inhalation when a nebulizer container is connected to portion 304. Thus, when no nebulizer container is coupled to portion 304, the open bottom end 306 of portion 304 permits ambient air to be drawn upwardly into portion 304, then through part of portion 302, and then past the first one-way valve 310 located at port 40. In some instances, therefore, the second one-way valve 316 may not open when a user inhales through port 30. However, when a nebulizer container is coupled to portion 304, ambient air is more apt to be drawn into portion 302 past one-way valve 316. This is especially the case if the user inhales air at a flow rate that exceeds the flow rate at which the pressure source of nebulizer 308 forces the nebulized or atomized breathable gas into portion 302 via portion 304 of connector 300.

When a person exhales, one-way valves 310, 316 both close and the persons exhaled breath is forced either through standard PEP device 100 or through oscillatory PEP device 200, depending upon the position of plug 44, as described above. Because valves 310, 316 are closed during the exhalation phase of the user's breathing cycle, the nebulized or atomized medication being forced into nebulizer connector 300 by the pressure source of nebulizer 308 is not lost to the ambient surrounding, thereby minimizing the waste of the liquid medication held by the associated nebulizer container of nebulizer 308. The nebulized gas that accumulates within connector 300 while valves 310, 316 are closed is then inhaled by the user during the next inhalation phase of the user's breathing cycle.

In the illustrative example, the first and second one-way valves 310, 316 are each umbrella valves in that they resemble the shape of an umbrella. Thus, each of valves 310, 316 has a dome-shaped portion 318 and a stem or rod portion 320 that extends away from an apex of the concave side of the dome-shaped portion. Only an enlarged distal end portion of stem 320 of valve 316 can be seen in FIG. 1, for example, because a cylindrical intermediate portion of stem 320 is situated in a hole extending through a central hub 322 that is supported relative to an annular end wall 324 of connector 300 by four spokes 326, shown in FIGS. 1 and 4. The first one-way valve 310 is mounted at port 40 by a similar hub and spoke arrangement. However, only two of the four spokes 326 can be seen in FIG. 1. During construction, the enlarged ends of stems 320 are forced through the holes in respective hubs 322 and thereafter, cooperate with dome-shaped portions 318 to prevent valves 310, 316 from inadvertently disconnecting from the associated hubs 320.

It is the dome shaped portions 318 of valves 310, 316 that move to open and close port 40 and the distal end of connector 300, as the case may be. When valves 310, 316 are open during the user's inhalation phase, ambient air or breathable gas with nebulized medication, as the case may be, moves through the somewhat pie-shaped windows defined by the four spokes 326, the associated hub 322, and either port 40 (in the case of valve 310) or annular end wall 324 (in the case of valve 316). In the illustrative example, first one-way valve 310 and the second one-way valve 316 are aligned with port 40. Thus, stems 320 of valves 310, 316 are collinear or coaxial with each other.

Based on the foregoing, it will be appreciated that nebulizer connector 300 of the illustrative embodiment includes a first tubular member that includes portions 302, 312, 314 carrying first one-way valve 310 at a first end and carrying the second one-way valve 316 at a second end. Illustrative nebulizer connector 300 also includes a second tubular member 304 that is perpendicular to the first tubular member and it is the second tubular member 304 that serves as a nebulizer port that is located between the first and second one-way valves 310, 316.

As indicated diagrammatically in FIGS. 2 and 3, a cosmetic cover or housing 330 optionally is provided to cover portions of standard PEP device 100, oscillatory PEP device 200, and nebulizer connector 300. Cover 330 is attached to housing 22 and is made up of multiple pieces in some embodiments. For example, cover 330 includes a clam shell type of structure in some embodiments. As shown in FIG. 3, at least a portion of knob 106 extends upwardly from the cover 330 and at least a portion of tubular member 304 extends downwardly beyond a bottom of the cover 330 to provide a user with access to these elements of device 20. Accordingly, cover 330 has appropriately sized openings through which knob 106 and tubular member 304 extend. Cover 330, if present, has small openings or apertures to permit air to move into and out of the interior region of cover 330 during the user's breathing cycle.

In some embodiments, an upper wall of cover 330 is situated above eccentric disk 124 and serves as the mechanism or means by which stem 110 is retained within stem receiver 108. That is, the upper wall of cover 330 prevents knob 106 and stem 108 from being inadvertently pulled upwardly relative to stem receiver 108. In other embodiments, a bottom end of stem 110 is formed with an annular flange or lip that snaps past the end of stem receiver 108 to retain knob 106 and stem 110 in place axially relative to stem receiver 108. In still other embodiments, a bottom end of stem 110 projects beyond the bottom end of stem receiver 108 and a snap ring, such as a C-ring or E-ring, is attached to projecting portion of stem 110 to retain stem 110 and knob 106 axially relative to stem receiver 108. In still other embodiments, an end cap is threaded into a bottom of stem 110 and includes a flange that extends radially outwardly beneath stem receiver 108 to retain stem 110 and knob 106 axially relative to stem receiver 108. In such embodiments, the end cap includes a bore or passage therethough so that the user's exhaled breath is able to escape from the standard PEP device 100.

Referring now to FIGS. 6-10, another embodiment of a respiratory therapy device 20' includes a housing 22 that is substantially the same as housing 22 of device 20. Nebulizer connector 300 of device 20' is also substantially the same as nebulizer connector 300 of device 20. Accordingly, the same reference numbers are used to denote portions of device 20' that are substantially the same as device 20 such that duplicative or redundant explanations of these elements or features of device 20' are not needed. For example, device 20' has a knob 46 that moves a valve member internal to housing 22 to open and close respective first and second ports 36', 38' in the same manner that knob 46 of device 20 moves valve member 44 to open and close ports 36, 38. Accordingly, the details of valve member 44 do not need to be shown and described again in connection with device 20' since the operation is the same.

Figure 6:
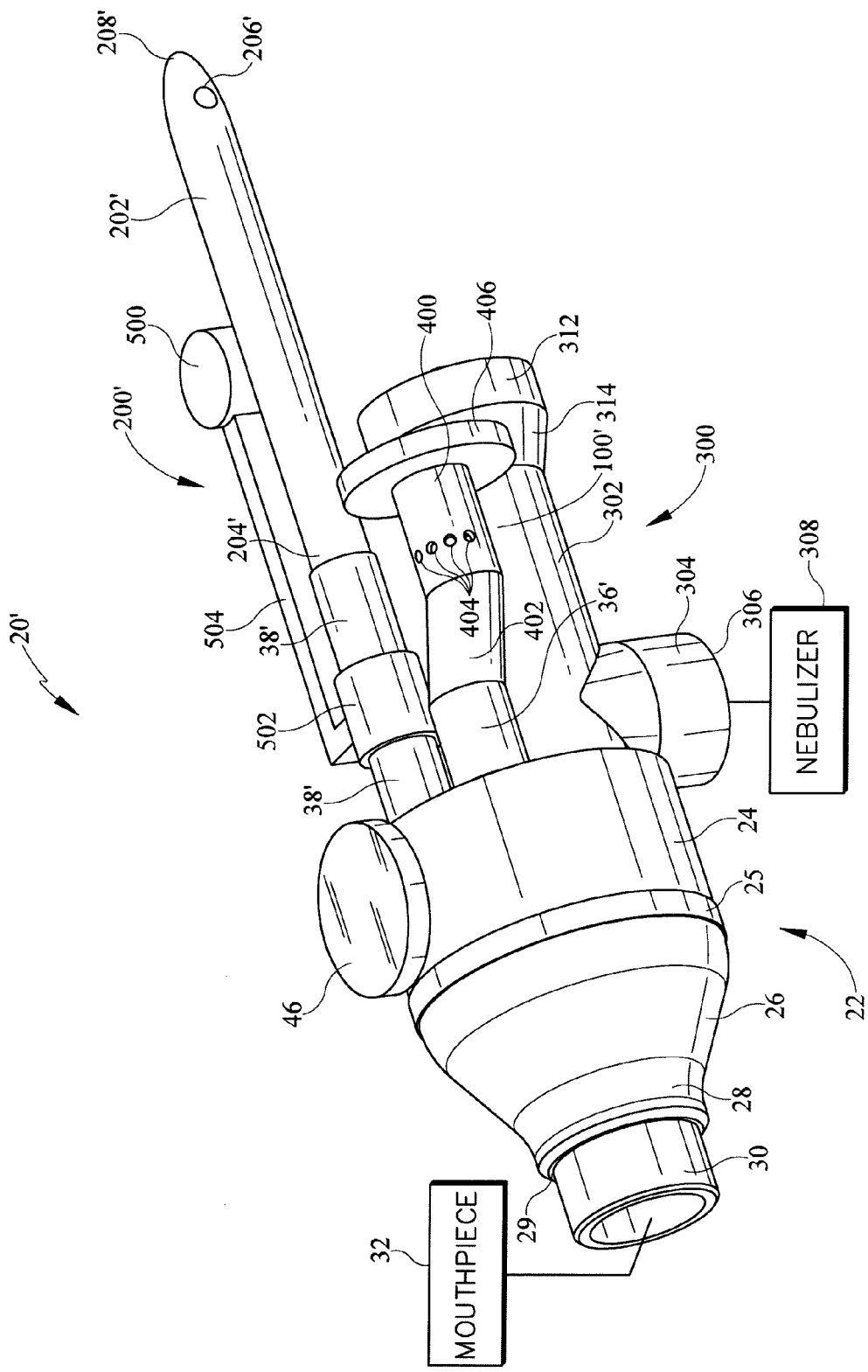
FIG. 6 is a perspective view of an alternative embodiment of a respiratory therapy device similar to the embodiment of FIG. 1 but having a slidable adjustment member with a fulcrum to change an oscillation characteristic of the oscillatory PEP device and having a knob of a standard PEP device situated adjacent a distal end of a tube of the standard PEP device and rotatable to block a varying number of apertures formed in the tube.
Figure 7:
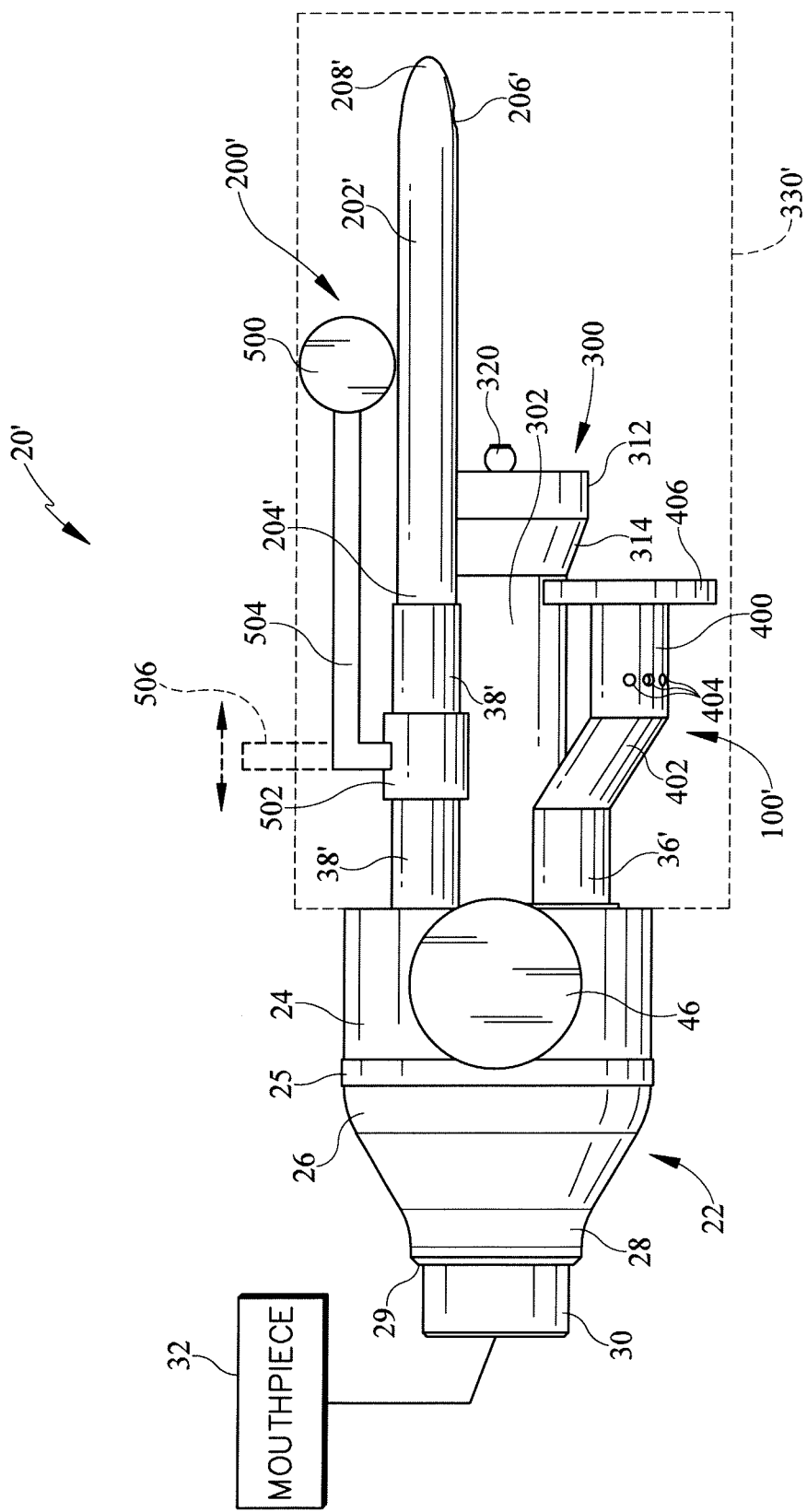
FIG. 7 is a top view of the respiratory therapy device of FIG. 6 showing a collar of the slidable adjustment member slid to a position about midway along a rigid tube extending from the third port and showing the fulcrum at a position about midway along a flexible tube of the oscillatory PEP device.
Figure 8:
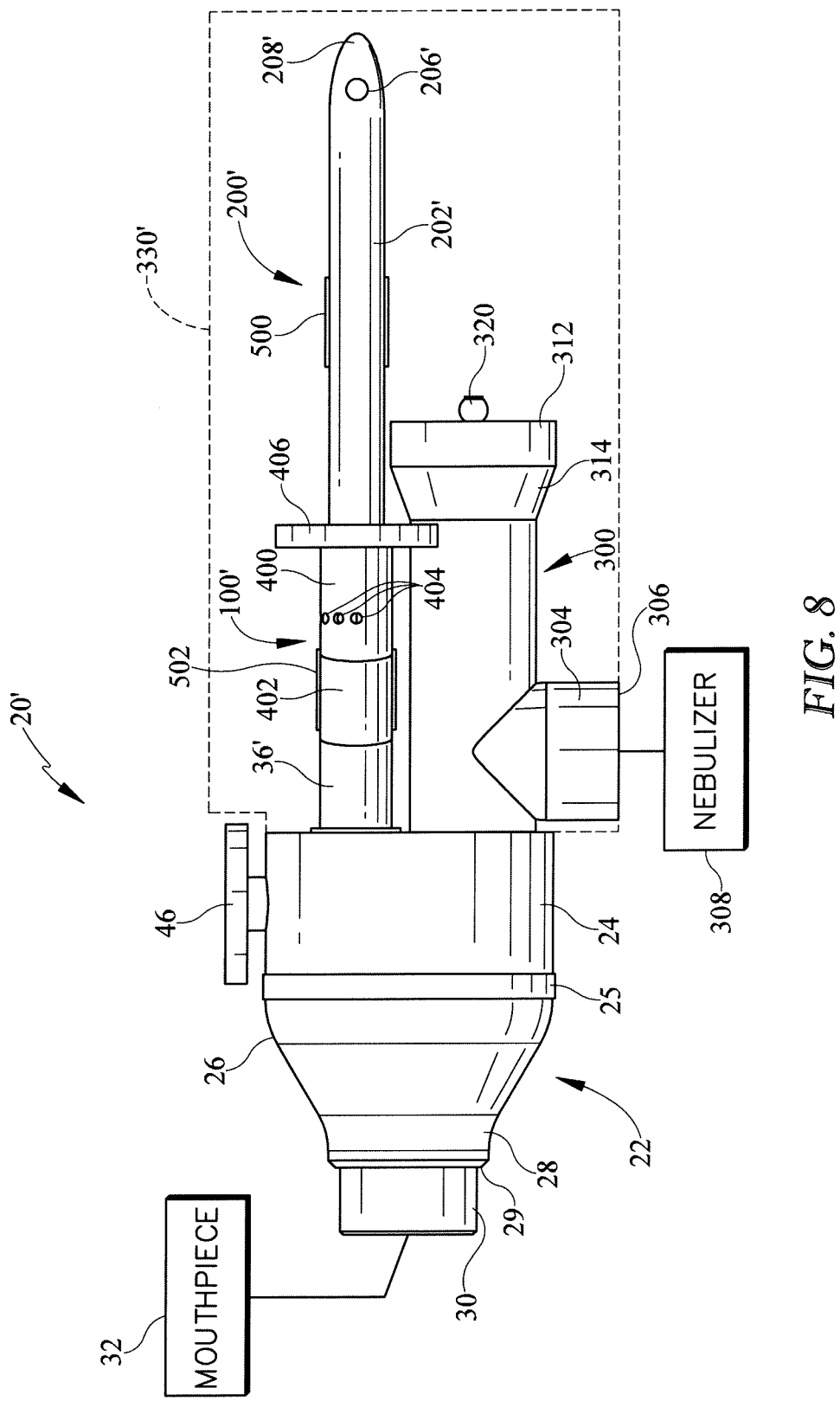
FIG. 8 is a side view of the respiratory therapy device of FIGS. 6 and 7.
Figure 9:
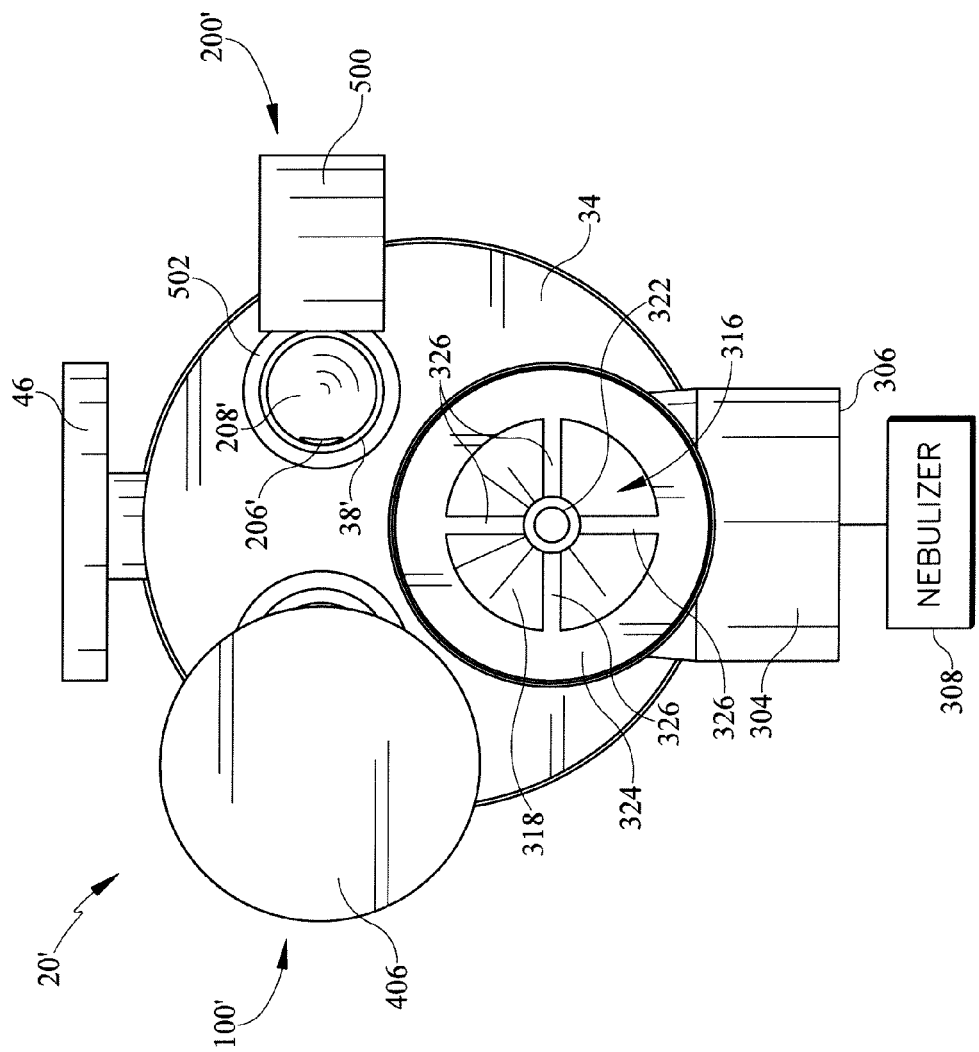
FIG. 9 is an end view of the respiratory therapy device of FIGS. 6-8 showing portions of a one-way valve exposed in a set of pie-shaped openings of a distal end of the nebulizer connector.

The main difference between device 20' and device 20 is the configuration of a standard PEP device 100' and an oscillatory PEP device 200' of respiratory therapy device 20' as compared to devices 100, 200 of respiratory therapy device 20. Standard PEP device 100' includes a distal tubular portion 400 coupled to port 36' by an intermediate tubular portion 402 as shown in FIGS. 6-8. Portion 400 is offset laterally by a slight amount with respect to port 36' and therefore, portion 402 is angled or inclined relative to port 36' and portion 400. When viewed from above, portion 402 appears to be a rhomboid (i.e., a quadrilateral whose opposite sides are parallel and adjacent sides are of unequal length, and whose angles are not right angles) as shown in FIG. 7.

In the illustrative embodiment of device 20', port 36' is longer than port 36 of device 20. Also, in some embodiments, port 36' and portions 400, 402 are molded integrally with each other and then attached to housing 22 via RF welding or adhesive or press fitting the proximal end of port 36' into an appropriately sized hold formed in end wall 34 of housing 22. In other embodiments, port 36' is integrally molded with housing 22 and then portions 400, 402 are formed as a single piece that attaches to the distal end of port 36' via RF welding or adhesive, for example. In still further embodiments, each of port 36', portion 400 and portion 402 are formed as a separate piece and then fastened together via RF welding or adhesive, for example.

Figure 10:
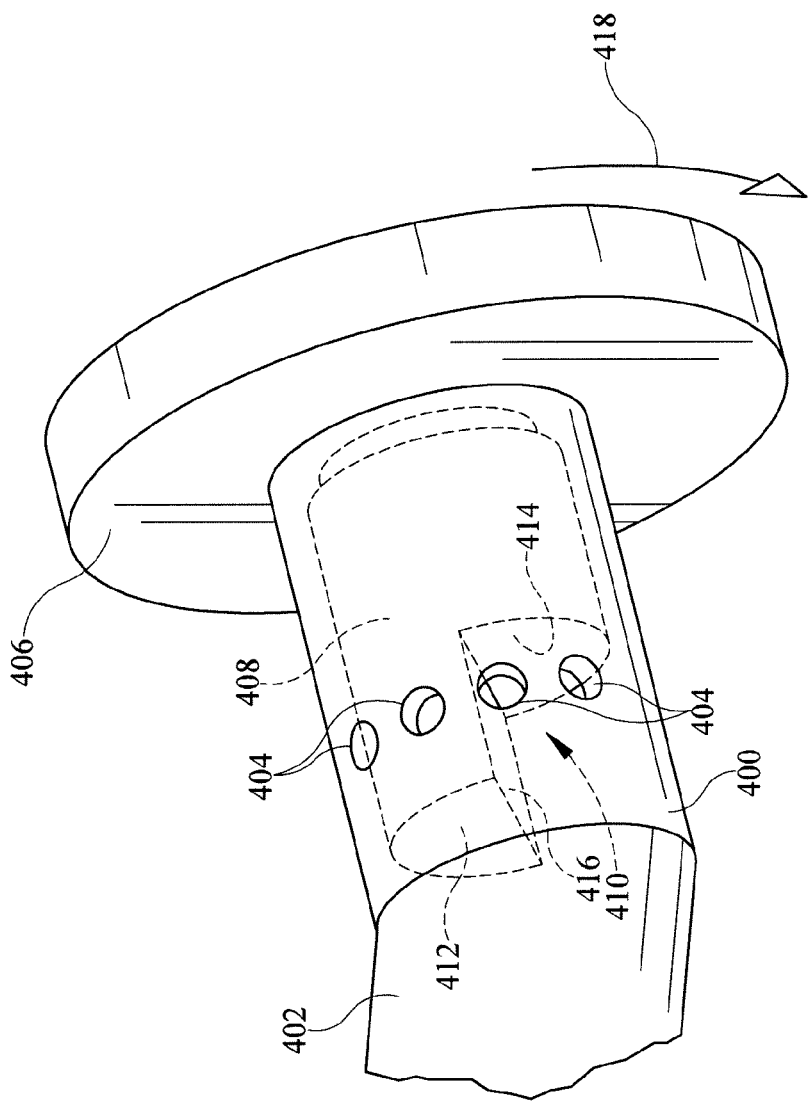
FIG. 10 is an enlarged perspective view of the distal end of the standard PEP device of the respiratory therapy device of FIGS. 6-9 showing the knob of the standard PEP device having a stem (in phantom) that is solid but with a D-shaped portion defined by a cutout that is rotatable to place a varying number of the set of apertures in communication with an interior region of the tube of the standard PEP device.

Portion 400 of standard PEP device 100' includes a plurality of apertures 404 that are circumferentially spaced thereabout as shown in FIGS. 6-8 and 10. Standard PEP device 100' further includes an adjuster or knob 406 and a stem 408 (FIG. 10) that is received in the interior region of tubular portion 400. An end of stem 408 spaced from knob 406 is formed with a cutout 410 as shown in FIG. 10 (in phantom). The cutout 410 extends axially about half the length of stem 408 and extends diametrically through stem 408. Thus, as a result of cutout 410, stem 408 has a D-shaped distal end surface 412, a D-shaped intermediate surface 414, and a rectangular surface 416 extending between D-shaped surfaces 412, 414 as shown in FIG. 10.

As knob 406 is turned, the number of apertures 404 blocked by stem 408 and the number of apertures 404 in pneumatic communication with cutout 410, and therefore with the interior passage of tubular portions 400, 402, changes. For example, in FIG. 10, two of apertures 404 are blocked by stem 408 and two of apertures 404 are unblocked. If knob 406 is turned in the direction of arrow 418 by a threshold amount, another one of apertures 404 will become blocked by stem 408 and then further rotation of knob 406 by another threshold increment will block the next adjacent aperture 404. Thus, in the illustrative example, there are four (4) apertures 404 and knob 406 is rotatable to positions blocking four or three or two or one or none of apertures 404. It will be appreciated that the more of apertures 404 that are blocked, the more resistance there is to a user's ability to exhale through standard PEP device 100' and that the less apertures 404 that are blocked, the less resistance there is to a user's ability to exhale through standard PEP device 100'.

Oscillatory PEP device 200' includes a flexible tube 202' having a first end 204' coupled to third port 38' as shown in FIGS. 6 and 7. Like flexible tube 202 of device 20, flexible tube 202' of device 20' is a somewhat torpedo or missile shaped hollow tube that, when not in use, extends in a straight, cantilevered manner from port 38' in parallel relation with tubular portion 400 of standard PEP device 100'. Flexible tube 202' has an opening 206' near a second end 208'. In use, a user's exhaled breath enters tube 202' through port 38' and moves generally longitudinally down the length of tube 202' and then exits opening 206' in a lateral direction or generally perpendicular to the longitudinal dimension of tube 202'. As the exhaled air exits opening 206' of tube 202', tube 202' flexes back and forth in an oscillatory manner. In some embodiments, tube 202' is made of a rubber material, for example, as was the case with regard to tube 202 of oscillatory PEP device 200 of device 20.

Oscillatory PEP device 200' includes a fulcrum 500 that is movable to change the oscillation characteristics of tube 202'. Thus, by changing the position of fulcrum 500 relative to tube 202', an amplitude and/or frequency at which flexible tube 202' oscillates is changed. In the illustrative embodiment of device 20', fulcrum 500 comprises a cylindrical member that is move along the length of tube 202' to change the point at which flexible tube 202' is able to flex in a first direction. Opening 206' is positioned such that the user's exhaled breath exits opening 206' and in a second direction opposite the first direction. That is opening 206' is located on the opposite side of tube 202' as that engaged by fulcrum 500.

In the illustrative embodiment, fulcrum 500 is larger in vertical height than the diameter of flexible tube 202' but this need not be the case. Device 200' also includes a collar 502 mounted on port 38' for sliding movement therealong and an L-shaped arm or connector 504 that interconnects collar 502 and fulcrum 500. Collar 500 is positioned around the outside of port 38' and tube 202' extends into port 38. Arm 504 and fulcrum 500 are sized and shaped so that when tube 202' is straight, a contact area on the outside surface of tube 202' is generally tangent to fulcrum 500.

As indicated diagrammatically in FIGS. 7 and 8, a cosmetic cover or housing 330' optionally is provided to cover portions of standard PEP device 100', oscillatory PEP device 200', and nebulizer connector 300 of device 20'. Cover 330' is attached to housing 22 and is made up of multiple pieces in some embodiments. For example, cover 330' includes a clam shell type of structure in some embodiments. As shown in phantom in FIG. 7, at least a portion of an adjuster or slider tab 506 extends past a side boundary of cover 330'. Tab 506 is formed integrally with collar 502 in some embodiments and is a separate piece that is fixed to collar 502 in other embodiments. The side boundary of cover 330' includes a slot through which tab 506 extends and along which tab 506 may be moved manually to adjust the position of collar 502 along port 38' and therefore, to adjust the position of fulcrum 500 along tube 202'. The width of the slot in cover 330' is only slightly larger than the width of tab 506 so that the receipt of tab 506 in the slot of cover 330' limits the ability of collar 502 to rotate on port 38'. Furthermore, the length of the slot in cover 330' insures that collar 502 is not inadvertently slid off of the end of port 38' because tab 506 will engage an end of the slot prior to collar 502 moving off of the distal end of port 38'.

It will be appreciated that at least a portion of knob 406 also extends beyond the boundary of cover 330', such as by extending through an opening or slot provided in cover 330' so that a user is able to manually engage and rotate knob 406 to adjust the operation of standard PEP device 100'. As was the case with cover 330, cover 330' has small openings or apertures to permit air to move into and out of the interior region of cover 330' during the user's breathing cycle. As shown in FIG. 8, a bottom of cover 330' is substantially coplanar with bottom 306 of portion 304 of nebulizer connector 300 in the illustrative example. However, cover 330' includes an opening to through which the nebulizer container of nebulizer 308 is inserted to mate with portion 304.

Although certain illustrative embodiments have been described in detail above, many embodiments, variations and modifications are possible that are still within the scope and spirit of this disclosure as described herein and as defined in the following claims.

The invention claimed is:

1. A respiratory therapy device comprising
a housing having a first port to receive a person's exhaled breath, a second port, and a third port,
a non-oscillatory positive expiratory pressure (PEP) device coupled to the second port,
an oscillatory PEP device coupled to the third port,
a manually operable valve member movable between a first position blocking the third port and allowing the person's exhaled breath to flow to the non-oscillatory PEP device through the second port and a second position blocking the second port and allowing the person's exhaled breath to flow to the oscillatory PEP device through the third port, wherein the non-oscillatory PEP device includes a tube, a knob, and a cylindrical stem extending from the knob, the cylindrical stem having a hollow central passage, an open end, and a plurality of apertures communicating with the hollow central passage, the stem being situated adjacent the tube and being movable to select how many of the plurality of apertures of the cylindrical stem are exposed to an interior region of the tube thereby to change a flow resistance of the non-oscillatory PEP device, and
an adjuster coupled to the knob, the adjuster engaging a member of the oscillatory PEP device to adjust a characteristic of oscillation of the oscillatory PEP device.

2. The respiratory therapy device of claim 1, wherein the non-oscillatory PEP device further comprises a stem receiver at an end of the tube, the stem is received in the stem receiver for rotation, the knob being situated adjacent one end of the stem receiver, and an opposite end of the stem receiver is open.

3. The respiratory therapy device of claim 1, wherein the tube comprises a first segment and a second segment that is perpendicular to the first segment.

4. The respiratory therapy device of claim 1, wherein the adjuster comprises an eccentric disk having an edge that engages the member.

5. The respiratory therapy device of claim 4, wherein the member has a detent and the edge of the eccentric disk has a plurality of notches, the detent indexing from notch to notch as the knob is rotated.

6. The respiratory therapy device of claim 1, wherein the oscillatory PEP device includes a flexible tube having a first end coupled to the third port, the flexible tube having an opening near a second end, and the oscillatory PEP device includes a stopper that is movable to change a frequency at which the flexible tube oscillates when the person's exhaled breath passes through the flexible tube and exits the opening.

7. The respiratory therapy device of claim 6, wherein the stopper comprises a flexible stick that is flexed by varying amounts to change the amount by which the flexible tube is able to flex in at least a first direction.

8. The respiratory therapy device of claim 7, wherein the person's exhaled breath exits the opening in the flexible tube toward the flexible stick.

9. The respiratory therapy device of claim 7, wherein the flexible stick is longer than the flexible tube.

10. The respiratory therapy device of claim 7, wherein the oscillatory PEP device includes a member coupled to the flexible stick, the member engaging an adjustment device of the non-oscillatory PEP device so that the same adjustment device is used to adjust operation of the non-oscillatory PEP device and the oscillatory PEP device.

11. The respiratory therapy device of claim 10, wherein the adjustment device includes a rotatable knob.

12. The respiratory therapy device of claim 1, wherein the housing has a fourth port and further comprising a nebulizer connector coupled to the fourth port.

13. The respiratory therapy device of claim 12, wherein the nebulizer connector has a first one-way valve located adjacent the fourth port, the first one-way valve normally being closed and adapted to open when the person inhales through the first port.

14. The respiratory therapy device of claim 13, wherein the nebulizer connector has a second one-way valve spaced from the first one-way valve, the second one-way valve normally being closed and adapted to open when the person inhales to permit ambient air to enter into an interior region of the nebulizer connector.

15. The respiratory therapy device of claim 14, wherein the first one-way valve and the second one-way valve are aligned with the third port.

16. The respiratory therapy device of claim 14, wherein the first and second one-way valves comprise umbrella valves.

17. The respiratory therapy device of claim 14, wherein the nebulizer connector includes a nebulizer port situated between the first and second one-way valves, the nebulizer port being adapted for coupling to a nebulizer.

18. The respiratory therapy device of claim 14, wherein the nebulizer connector includes a first tubular member carrying the first one-way valve at a first end and carrying the second one-way valve at a second end and the nebulizer connector includes a second tubular member that is perpendicular to the first tubular member, the second tubular member serving as the nebulizer port.

19. A respiratory therapy device comprising
a housing having a first port to receive a person's exhaled breath generally along a flow path, the housing having an end wall spaced from the first port and arranged generally perpendicular to the flow path, the end wall having a second port, a third port, and a fourth port,
a non-oscillatory positive expiratory pressure (PEP) device coupled to the second port,
an oscillatory PEP device coupled to the third port,
a nebulizer connector coupled to the fourth port,
a first manually operable member that is movable to select whether the first port communicates with the non-oscillatory PEP device through the second port or whether the first port communicates with the oscillatory PEP device through the third port, and
a second manually operable member that is movable to adjust operation of at least one of the non-oscillatory PEP device and the oscillatory PEP device, wherein the second manually operable member comprises a rotatable knob having a first portion that adjusts operation of the non-oscillatory PEP device when the knob is rotated and a second portion that adjusts operation of the oscillatory PEP device when the knob is rotated.

20. The respiratory therapy device of claim 19, wherein the first portion comprises a cylindrical stem having a hollow core and a plurality of apertures extending through the cylindrical stem.

21. The respiratory therapy device of claim 19, wherein the second portion comprises a disk.

22. The respiratory therapy device of claim 21, wherein the disk is eccentric to an axis about which the knob rotates.

23. The respiratory therapy device of claim 22, wherein the disk includes an edge having notches that selectively receive an adjustment member of the oscillatory PEP device when the respective notch is aligned with the adjustment member.

24. The respiratory therapy device of claim 23, wherein the oscillatory PEP device includes a flexible tube and movement of the adjustment member by the disk changes a characteristic of oscillation of the flexible tube.

25. The respiratory therapy device of claim 24, wherein the characteristic of oscillation changed by movement of the disk comprises at least one of a frequency of oscillation and an amplitude of oscillation.

26. The respiratory therapy device of claim 23, wherein the oscillatory PEP device includes an elongated stick coupled to the adjustment device and extending alongside the flexible tube, the adjustment device being formed as a tab extending from the elongated stick.

27. The respiratory therapy device of claim 19, wherein the first manually operable member comprises a knob, a stem extending from the knob, and a plug coupled to the stem.

28. The respiratory therapy device of claim 27, wherein the plug comprises a first end that blocks the second port from communicating with the first port when the knob is rotated to a first position and the plug comprises a second end that blocks the third port from communicating with the first port when the knob is rotated to a second position.

29. The respiratory therapy device of claim 28, wherein the first and second ends of the plug are tapered.

30. The respiratory therapy device of claim 28, wherein the first and second ends of the plug are substantially conical.

31. The respiratory therapy device of claim 28, wherein the knob rotates through about 180 degrees when moving between the first and second positions.

32. The respiratory therapy device of claim 28, wherein the knob and stem rotate about a first axis and the plug is shaped to define a second axis extending between the first and second ends, the second axis being orthogonal to the first axis.

33. The respiratory therapy device of claim 27, wherein the plug is coupled to the stem by a tab that positions the plug in offset relation with the stem.

34. The respiratory therapy device of claim 19, wherein the end wall is circular and the housing further comprises a cylindrical wall extending from the end wall toward the first port and defining a chamber adjacent the second, third, and fourth ports and wherein the first manually operable member comprises a knob situated outside the chamber, a stem that extends from the knob into the chamber through the cylindrical wall, and a plug situated inside the chamber.

35. The respiratory therapy device of claim 19, wherein the nebulizer connector comprises a T-shaped connector having a first tubular segment with a first end that connects to the fourth port and a second end spaced from the first end, the T-shaped connector having a second tubular segment extending from the first segment in perpendicular relation therewith, and the second segment having an open end sized to couple to a nebulizer container.

36. The respiratory therapy device of claim 35, wherein at least one of the first and second ends of the first segment of the T-shaped connector carry a one-way valve.

37. The respiratory therapy device of claim 36, wherein both of the first and second ends of the first segment of the T-shaped connector carry a one-way valve.

38. The respiratory therapy device of claim 35, wherein the one-way valve comprises an umbrella valve.

39. The respiratory therapy device of claim 35, wherein the one-way valve is normally closed and is adapted to open in response to a person's inhalation through the first port.

40. A respiratory therapy device comprising
a housing having a first port to receive a person's exhaled breath and the housing having an interior region,
a non-oscillatory positive expiratory pressure (PEP) device coupled to the housing and having a first passage that selectively communicates with the interior region of the housing,
an oscillatory PEP device coupled to the housing and having a second passage that selectively communicates with the interior region of the housing,
at least one selector that is movable to select whether the non-oscillatory PEP device or the oscillatory PEP device is in communication with the interior region of the housing, and
at least one adjuster that is movable to adjust the operation of at least one of the non-oscillatory PEP device and the oscillatory PEP device, wherein the at least one adjuster includes a single knob that is rotatable to adjust the operation of both the non-oscillatory PEP device and the oscillatory PEP device.

41. The respiratory therapy device of claim 40, further comprising a nebulizer connector coupled to the housing and having a first one-way valve that is normally being closed and that is adapted to open when a person inhales through the first port.

42. A respiratory therapy device comprising
a housing having a first port to receive a person's exhaled breath, a second port, and a third port,
a non-oscillatory positive expiratory pressure (PEP) device coupled to the second port,
an oscillatory PEP device coupled to the third port, and
a manually operable valve member movable between a first position blocking the third port and allowing the person's exhaled breath to flow to the non-oscillatory PEP device through the second port and a second position blocking the second port and allowing the person's exhaled breath to flow to the oscillatory PEP device through the third port,
wherein the oscillatory PEP device includes a flexible tube having a first end coupled to the third port, the flexible tube having an opening near a second end, and the oscillatory PEP device includes a stopper that is movable to change a frequency at which the flexible tube oscillates when the person's exhaled breath passes through the flexible tube and exits the opening,
wherein the stopper comprises a flexible stick that is flexed by varying amounts to change the amount by which the flexible tube is able to flex in at least a first direction,
wherein the oscillatory PEP device includes a member coupled to the flexible stick, the member engaging an adjustment device of the non-oscillatory PEP device so that the same adjustment device is used to adjust operation of the non-oscillatory PEP device and the oscillatory PEP device.

43. The respiratory therapy device of claim 42, wherein the adjustment device includes a rotatable knob.

\* \* \* \* \*

UNITED STATES PATENT AND TRADEMARK OFFICE
CERTIFICATE OF CORRECTION

PATENT NO. : 9,180,271 B2
APPLICATION NO. : 13/411679
DATED : November 10, 2015
INVENTOR(S) : Mike Yang Chang Guo et al.

It is certified that error appears in the above-identified patent and that said Letters Patent is hereby corrected as shown below:

On the title page item 75

Replace Inventor Radhakrishnan Nair Oravelil Kamalashi's name, replacing "Oravielil" with --Oravelil--.

Signed and Sealed this
Third Day of May, 2016

Michelle K. Lee
*Director of the United States Patent and Trademark Office*